(12) United States Patent
Gerken et al.

(10) Patent No.: US 11,845,747 B2
(45) Date of Patent: *Dec. 19, 2023

(54) ESTER AND CARBONATE PYRIMIDINE COMPOUNDS AS JAK KINASE INHIBITORS

(71) Applicant: THERAVANCE BIOPHARMA R&D IP, LLC, South San Francisco, CA (US)

(72) Inventors: Philip A. Gerken, San Francisco, CA (US); Jianhua Chao, Palo Alto, CA (US); Daniel D. Long, San Francisco, CA (US)

(73) Assignee: THERAVANCE BIOPHARMA R&D IP, LLC, South San Francisco, CA (US)

( * ) Notice: Subject to any disclaimer, the term of this patent is extended or adjusted under 35 U.S.C. 154(b) by 137 days.

This patent is subject to a terminal disclaimer.

(21) Appl. No.: 17/448,922

(22) Filed: Sep. 27, 2021

(65) Prior Publication Data
US 2022/0009926 A1 Jan. 13, 2022

Related U.S. Application Data

(63) Continuation of application No. 16/856,280, filed on Apr. 23, 2020, now Pat. No. 11,155,549.

(60) Provisional application No. 62/837,829, filed on Apr. 24, 2019.

(51) Int. Cl.
| | | |
|---|---|---|
| *A61K 31/506* | (2006.01) | |
| *C07D 471/08* | (2006.01) | |
| *A61P 17/14* | (2006.01) | |
| *A61P 17/04* | (2006.01) | |
| *A61K 9/00* | (2006.01) | |
| *A61K 9/06* | (2006.01) | |
| *A61K 45/06* | (2006.01) | |

(52) U.S. Cl.
CPC ............ *C07D 471/08* (2013.01); *A61P 17/04* (2018.01); *A61P 17/14* (2018.01); *A61K 9/0014* (2013.01); *A61K 9/06* (2013.01); *A61K 45/06* (2013.01)

(58) Field of Classification Search
CPC ..................................................... A61K 31/506
USPC ........................................................ 514/272
See application file for complete search history.

(56) References Cited

U.S. PATENT DOCUMENTS

| | | |
|---|---|---|
| 6,653,300 B2 | 11/2003 | Bebbington et al. |
| 6,660,731 B2 | 12/2003 | Bebbington et al. |
| 6,664,247 B2 | 12/2003 | Bebbington et al. |
| 7,531,536 B2 | 5/2009 | Bebbington et al. |
| 7,625,913 B2 | 12/2009 | Bebbington et al. |
| 7,691,853 B2 | 4/2010 | Bebbington et al. |
| 7,951,820 B2 | 5/2011 | Bebbington et al. |
| 8,222,256 B2 | 7/2012 | Zhang |
| 8,815,877 B2 | 8/2014 | Aliagas-Martin et al. |
| 9,725,470 B2 | 8/2017 | Hudson et al. |
| 10,028,960 B2 | 7/2018 | Hudson et al. |
| 10,308,646 B2 | 6/2019 | Kozak et al. |
| 10,485,803 B2 | 11/2019 | Huang |
| 10,562,894 B2 | 2/2020 | Kozak et al. |
| 10,774,080 B2 | 9/2020 | Kozak et al. |
| 11,110,095 B2 | 9/2021 | Hudson et al. |
| 11,155,549 B2 * | 10/2021 | Gerken ................ C07D 471/08 |
| 2008/0004302 A1 | 1/2008 | Theoclitou et al. |
| 2009/0312543 A1 | 12/2009 | Bebbington et al. |
| 2016/0052930 A1 | 2/2016 | Fensome et al. |
| 2016/0347772 A1 | 12/2016 | Hudson et al. |
| 2020/0046709 A1 | 2/2020 | Hudson et al. |

(Continued)

FOREIGN PATENT DOCUMENTS

| | | |
|---|---|---|
| CN | 113372351 A | 9/2021 |
| CN | 113372364 A | 9/2021 |
| WO | 2007/059299 A1 | 5/2007 |

(Continued)

OTHER PUBLICATIONS

Abcouwer, "Angiogenic factors and cytokines in diabetic retinopathy", J Clin Cell Immunol, Supplement 1: 1-12 (2013).

(Continued)

*Primary Examiner* — Charanjit Aulakh
(74) *Attorney, Agent, or Firm* — Sheppard Mullin Richter & Hampton LLP

(57) ABSTRACT

The invention provides compounds of formula (I):

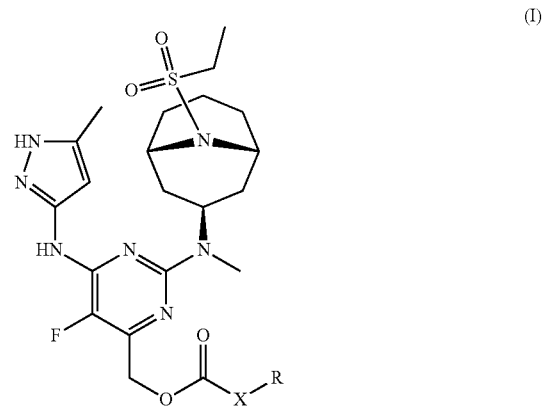

(I)

or pharmaceutically-acceptable salts thereof, that are inhibitors of Janus kinases and release an active metabolite in vivo. The invention also provides pharmaceutical compositions comprising such compounds, and methods of using such compounds to treat inflammatory skin diseases and other diseases.

17 Claims, No Drawings

(56) References Cited

U.S. PATENT DOCUMENTS

2020/0338073 A1 10/2020 Gerken et al.
2020/0339580 A1 10/2020 Gerken et al.

FOREIGN PATENT DOCUMENTS

| WO | 2008/005538 A2 | 1/2008 |
|---|---|---|
| WO | 2013/092940 A1 | 6/2013 |
| WO | 2015/094803 A1 | 6/2015 |
| WO | 2020/108516 A1 | 6/2020 |
| WO | 2020/108613 A1 | 6/2020 |

OTHER PUBLICATIONS

Baliwag et al., "Cytokines in psoriasis", Cytokine, 73(2): 342-350 (Jun. 2015).
Bao et al., "The involvement of the JAK-STAT signaling pathway in chronic inflammatory skin disease atopic dermatitis", JAK-STAT, 2(3): e24137-1-e24137-8 (2013).
Coghill et al., "Effector CD4+ T cells, the cytokines they generate, and GVHD: something old and something new", Blood, 117(12): 3268-3276 (Mar. 24, 2011).
Craiglow et al., "Tofacitinib citrate for the treatment of vitiligo: A pathogenesis-directed therapy", JAMA Dermatology, 151: 1110-1112 (2015).
Danese, "New therapies for inflammatory bowel disease: from the bench to the bedside", Gut, 61: 918-932 (2012).
De Nitto et al., "Involvement of interleukin-15 and interleukin-21, two gamma-chain-related cytokines, in celiac disease", World J Gastroenterol, 15(37): 4609-4614 (Oct. 7, 2009).
Feliciani et al., "A TH2-like cytokine response is involved in bullous pemphigoid. The role of IL-4 and IL-5 in the pathogenesis of the disease", International Journal of Immunopathology and Pharmacology, 12(2): 55-61 (1999).
Horai et al, "Cytokines in autoimmune uveitis", Journal of Interferon & Cytokine Research, 31(10): 733-744 (2011).
Ishizaki et al., "Involvement of tyrosine kinase-2 in both the IL-12/Th1 and IL-23/Th17 axes in vivo", J Immunol, 187: 181-189 (2011).
Knickelbein et al., "Inflammatory mechanisms of age-related macular degeneration", International Ophthalmology Clinics, 55(3): 63-78 (2015).
Kozak, "Discovery and profiling of novel, intestinally-restricted oral pan-JAK inhibitors for the treatment of Inflammatory bowel diseases", (Apr. 2017).
Kozak, "Discovery and profiling of novel, intestinally-restricted oral pan-JAK inhibitors for the treatment of Inflammatory bowel diseases", (Jun. 2017).
Kozak et al., "Discovery and profiling of novel, intestinally-restricted oral pan-JAK inhibitors for the treatment of Inflammatory bowel diseases", Poster at the Gordon Research Conference (Aug. 6-11, 2017).
Kudlacz et al., "The JAK-3 inhibitor CP-690550 is a potent anti-inflammatory agent in a murine model of pulmonary eosinophilia", European Journal of Pharmacology, 582: 154-161 (2008).
Kumawat et al., "Microscopic colitis patients demonstrate a mixed Th17/Tc17 and Th1/Tc1 mucosal cytokine profile", Molecular Immunology, 55: 355-364 (2013).
Leung et al., "New insights into atopic dermatitis", J Clin Invest, 113(5): 651-657 (2004).
Malaviya et al., "Janus Kinase-3 dependent inflammatory responses in allergic asthma", International Immunopharmacology, 10: 829-836 (2010).
Matsunaga et al., "Effects of a Janus kinase inhibitor, pyridone 6, on airway responses in a murine model of asthma", Biochemical and Biophysical Research Communications, 404: 261-267 (2011).
Mozaffari et al., "New biologic therapeutics for ulcerative colitis and Crohn's disease", Expert Opin Biol Ther, 14(5): 583-600 (2014).
Netchiporouk et al., "Deregulation in STAT signaling is important for cutaneous T-cell lymphoma (CTCL) pathogenesis and cancer progression", Cell Cycle, 13(21): 3331-3335 (Nov. 1, 2014).
Okiyama et al., "Reversal of CD8 T-cell-mediated mucocutaneous graft-versus-host-like disease by the JAK inhibitor tofacitinib", Journal of Investigative Dermatology, 134: 992-1000 (2014).
Reimund et al., "Mucosal inflammatory cytokine production by intestinal biopsies in patients with ulcerative colitis and Crohn's disease", Journal of Clinical Immunology, 16(3): 144-150 (1996).
Schadler et al., "Biologics for the primary care physician: Review and treatment of psoriasis", Disease-a-month, 000: 1-40 (2018).
Shchuko et al., "Intraocular cytokines in retinal vein occlusion and its relation to the efficiency of anti-vascular endothelial growth factor therapy", Indian Journal of Ophthalmology, 63(12): 905-911 (2015).
Sohn et al., "Changes in aqueous concentrations of various cytokines after intravitreal triamcinolone versus bevacizumab for diabetic macular edema", Ophthalmology, 152: 686-694 (2011).
Sonkoly et al., "IL-31: A new link between T cells and pruritus in atopic skin inflammation", J Allergy Clin Immunol, 117(2): 411-417 (2006).
Stallmach et al., "Cytokine/chemokine transcript profiles reflect mucosal inflammation in Crohn's disease", Int J Colorectal Dis, 19: 308-315 (2004).
STELLAR_Partnering slides (2019).
Stevenson et al., "Dry eye disease", Arch Ophthalmol, 130(1): 90-100 (Jan. 2012).
Tanaka et al., "New insight into mechanisms of pruritus from molecular studies on familial primary localized cutaneous amyloidosis", British Journal of Dermatology, 161: 1217-1224 (2009).
Weinbrand-Goichberg et al., "Eosinophilic esophagitis: an immune-mediated esophageal disease", Immunol Res, 56: 249-260 (2013).
Welz-Kubiak et al., "IL-31 is overexpressed in lichen planus but its level does not correlate with pruritus severity", Journal of Immunology Research, Article 854747, 6 pages (2015).
Woywodt et al., "Mucosal cytokine expression, cellular markers and adhesion molecules in inflammatory bowel disease", European Journal of Gastroenterology & Hepatology, 11: 267-276 (1999).
Xing et al., "Alopecia areata is driven by cytotoxic T lymphocytes and is reversed by JAK inhibition", Nature Medicine, 20(9): 1043-1049 (Sep. 2014).
Yamamoto et al., "Mucosal inflammation in the terminal ileum of ulcerative colitis patients: Endoscopic findings and cytokine profiles", Digestive and Liver Disease, 40: 253-259 (2008).
Yano et al., "Ipilimumab augments antitumor activity of bispecific antibody-armed T cells", Journal of Translational Medicine, 12: 191 (2014).
Zhou et al., "Cytokines and Behcet's Disease", Autoimmunity Reviews, 11: 699-704 (2012).

* cited by examiner

ESTER AND CARBONATE PYRIMIDINE COMPOUNDS AS JAK KINASE INHIBITORS

CROSS-REFERENCE TO RELATED APPLICATIONS

This application is a continuation of U.S. Ser. No. 16/856,280, filed on Apr. 23, 2020, now U.S. Pat. No. 11,155,549, which application claims the benefit of U.S. Provisional Application No. 62/837,829, filed on Apr. 24, 2019, the disclosures of which are incorporated herein by reference in their entireties.

BACKGROUND OF THE INVENTION

Field of the Invention

The invention is directed to ester and carbonate pyrimidine compounds useful as JAK inhibitors which also release an active metabolite in vivo. The invention is also directed to pharmaceutical compositions comprising such compound, and methods of using such compounds to treat inflammatory and autoimmune diseases.

State of the Art

Inhibition of the family of JAK enzymes inhibits signaling of many key pro-inflammatory cytokines. Thus, JAK inhibitors are expected to be useful in the treatment of atopic dermatitis and other inflammatory skin diseases. Atopic dermatitis (AD) is a common chronic inflammatory skin disease that affects an estimated 14 million people in the United States alone. It is estimated that AD affects 10 to 20% of children and 1 to 3% of adults in developed countries (Bao et al., *JAK-STAT,* 2013, 2, e24137) and the prevalence is increasing. Elevation of proinflammatory cytokines that rely on the JAK-STAT pathway, in particular, IL-4, IL-5, IL-10, IL-12, IL-13, IFNγ, and TSLP has been associated with AD (Bao et al., Leung et al., *The Journal of Clinical Investigation,* 2004, 113, 651-657). In addition, upregulation of IL-31, another cytokine that signals through a JAK pairing, has been shown to have a role in the pruritus associated with the chronic state of AD (Sonkoly et al., *Journal of Allergy and Clinical Immunology,* 2006, 117, 411-417).

Due to the modulating effect of the JAK/STAT pathway on the immune system, systemic exposure to JAK inhibitors may have an adverse systemic immunosuppressive effect. Therefore, it would be desirable to provide new JAK inhibitors which have their effect at the site of action without significant systemic effects. In particular, for the treatment of inflammatory skin diseases, such as atopic dermatitis, it would be desirable to provide new JAK inhibitors which can be administered topically and achieve therapeutically relevant exposure in the skin. There remains a need for JAK inhibitor compounds with adequate solubility in aqueous and/or organic excipients allowing development of formulations for topical application.

SUMMARY OF THE INVENTION

In one aspect, the invention provides compounds having activity as a JAK inhibitors that also release an active metabolite in vivo.

Accordingly, the invention provides a compound of formula (I):

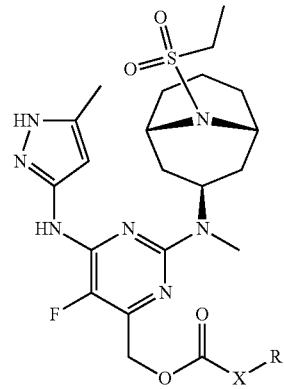

or a pharmaceutically-acceptable salt thereof, wherein X is —O— or a bond;

R is selected from the group consisting of a $C_{1-8}$ alkyl, a 4 to 7 membered heterocyclic group, and a 3 to 8 membered cycloalkyl group, wherein the $C_{1-8}$ alkyl, heterocyclic and cycloalkyl groups are optionally substituted with 1 to 3 $R^a$;

wherein each $R^a$ is independently selected from the group consisting of $C_{1-4}$ alkyl, CN, F, OH, $C_{1-4}$ alkyl-OH, and $C_{1-4}$ alkoxy.

The invention also provides a pharmaceutical composition comprising a compound of formula (I), or a pharmaceutically-acceptable salt thereof and a pharmaceutically-acceptable carrier.

The invention also provides a compound of formula (I) or a pharmaceutically-acceptable salt thereof for use as a medicament.

The invention also provides a compound of formula (I) or a pharmaceutically-acceptable salt thereof as described herein for use in treating inflammatory and autoimmune diseases or disorders.

The invention also provides a compound of formula (I) or a pharmaceutically-acceptable salt thereof for use in treating a disease in a mammal for which a JAK inhibitor is indicated.

The invention also provides a method of treating a disease in a mammal for which a JAK inhibitor is indicated, the method comprising administering a compound of formula (I), or a pharmaceutically acceptable salt thereof, to the mammal.

The invention also provides a method of treating inflammatory and autoimmune diseases of the skin in a mammal, in particular atopic dermatitis and alopecia areata, the method comprising administering compound (I), or a pharmaceutically acceptable salt thereof, to the mammal.

DETAILED DESCRIPTION OF THE INVENTION

Among other aspects, the invention provides compounds of formula (I), and pharmaceutically-acceptable salts thereof, having activity as JAK inhibitors which also release an active metabolite.

The invention provides a compound of formula (I):

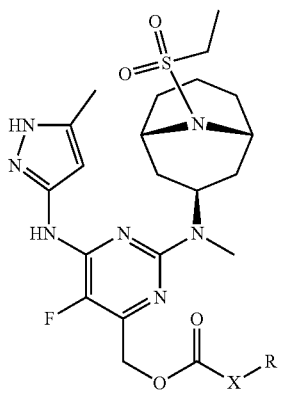

or a pharmaceutically-acceptable salt thereof,
wherein X is —O— or a bond;
R is selected from the group consisting of a $C_{1-8}$ alkyl, a 4 to 7 membered heterocyclic group, and a 3 to 8 membered cycloalkyl group, wherein the $C_{1-8}$ alkyl, heterocyclic and cycloalkyl groups are optionally substituted with 1 to 3 $R^a$;
each $R^a$ is independently selected from the group consisting of $C_{1-4}$ alkyl, CN, F, OH, $C_{1-4}$ alkyl-OH, and $C_{1-4}$ alkoxy.

In some embodiments, R is selected from the group consisting of a $C_{1-6}$ alkyl, a 5 to 7 membered heterocyclic group, and a 5 to 7 membered cycloalkyl group, wherein the $C_{1-6}$ alkyl, heterocyclic and cycloalkyl groups are optionally substituted with 1 to 3 $R^a$.

In some embodiments, R is selected from the group consisting of a $C_{1-6}$ alkyl, a 5 to 6 membered heterocyclic group, and a 5 to 6 membered cycloalkyl group, wherein the $C_{1-6}$ alkyl, heterocyclic and cycloalkyl groups are optionally substituted with 1 to 3 $R^a$.

In some embodiments, R is selected from the group consisting of $C_{1-6}$ alkyl, cyclohexyl, and tetrahydropyran, wherein the $C_{1-6}$ alkyl, cyclohexyl, and tetrahydropyran are optionally substituted with 1 to 2 $R^a$.

In some embodiments, R is selected from the group consisting of unsubstituted $C_{1-6}$ alkyl, unsubstituted cyclohexyl, and unsubstituted tetrahydropyran.

In some embodiments, R is selected from the group consisting of methyl, ethyl, isopropyl, propyl, n-butyl, n-hexyl, cyclohexyl, and tetrahydropyran.

In some embodiments, R is $C_{1-8}$ alkyl optionally substituted with 1 to 3 $R^a$.

In some embodiments, R is a 5 to 7 membered heterocyclic group optionally substituted with 1 to 3 $R^a$.

In some embodiments, R is a 5 to 7 membered cycloalkyl group optionally substituted with 1 to 3 $R^a$.

In some embodiments, X is a bond. In some embodiments, X is —O—.

In some embodiments, X is a bond and R is selected from the group consisting of a $C_{1-8}$ alkyl and a 4 to 7 membered heterocyclic group, wherein the $C_{1-8}$ alkyl and heterocyclic groups are optionally substituted with 1 to 3 $R^a$, wherein each $R^a$ is independently selected from the group consisting of $C_{1-4}$ alkyl, CN, F, OH, $C_{1-4}$ alkyl-OH, and $C_{1-4}$ alkoxy.

In some embodiments, X is a bond and R is selected from the group consisting of $C_{1-6}$ alkyl and tetrahydropyran, wherein the $C_{1-6}$ alkyl and tetrahydropyran are optionally substituted with 1 to 2 $R^a$.

In some embodiments, X is a bond and R is selected from the group consisting of methyl, ethyl, propyl, n-butyl, n-hexyl, and tetrahydropyran.

In some embodiments, X is —O— and R is selected from the group consisting of a $C_{1-6}$ alkyl, a 4 to 7 membered heterocyclic group, and a 3 to 8 membered cycloalkyl group, wherein the $C_{1-6}$ alkyl, heterocyclic and cycloalkyl groups are optionally substituted with 1 to 3 $R^a$, wherein each $R^a$ is independently selected from the group consisting of $C_{1-4}$ alkyl, CN, F, OH, $C_{1-4}$ alkyl-OH, and $C_{1-4}$ alkoxy.

In some embodiments, X is —O— and R is selected from the group consisting of a 4 to 7 membered heterocyclic group and a 3 to 8 membered cycloalkyl group, wherein the heterocyclic and cycloalkyl groups are optionally substituted with 1 to 3 $R^a$, wherein each $R^a$ is independently selected from the group consisting of $C_{1-4}$ alkyl, CN, F, OH, $C_{1-4}$ alkyl-OH, and $C_{1-4}$ alkoxy.

In some embodiments, X is —O— and R is selected from the group consisting of a 5 to 6 membered heterocyclic group, and a 5 to 6 membered cycloalkyl group, wherein the heterocyclic and cycloalkyl groups are optionally substituted with 1 to 3 $R^a$.

In some embodiments, X is —O— and R is selected from the group consisting of isopropyl, cyclohexyl, and tetrahydropyran.

The invention also provides a compound selected from the group consisting of:

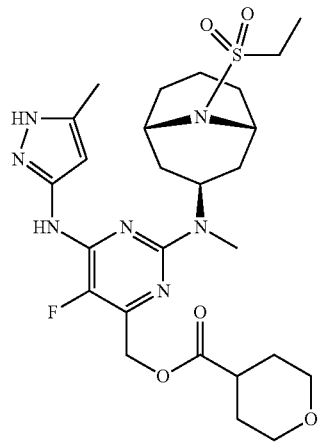

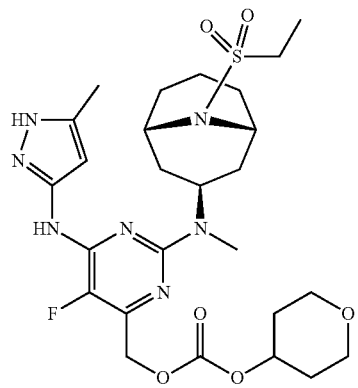

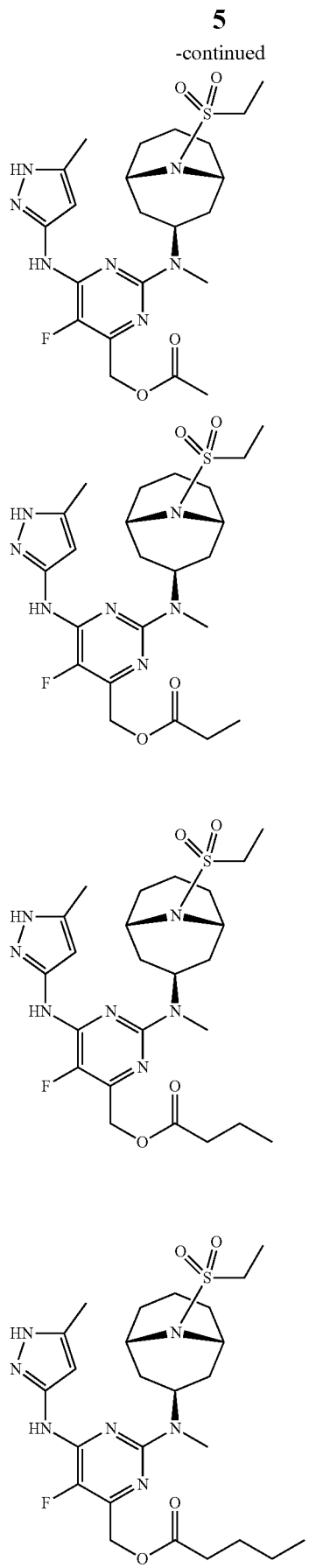
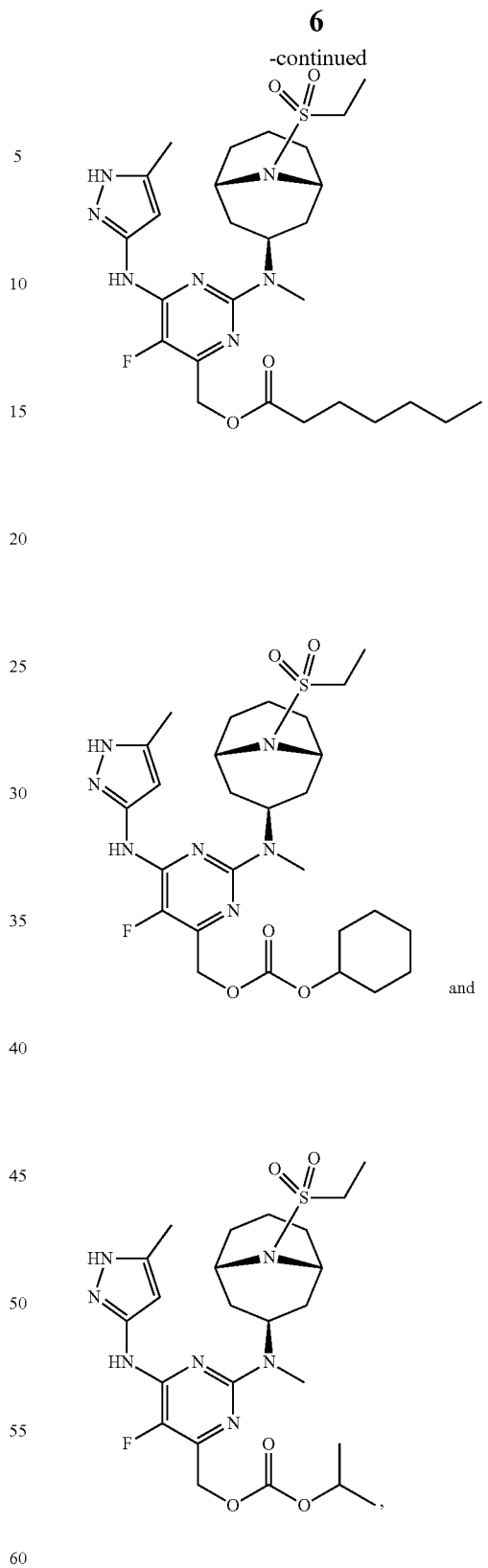
or a pharmaceutically acceptable salt thereof.
In some embodiments, the compound is a compound of formula:

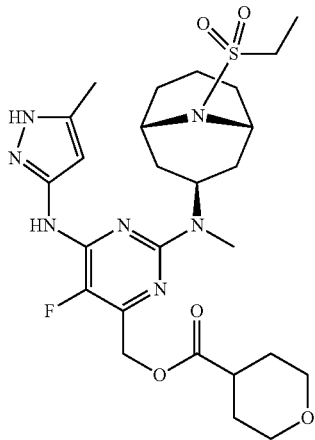

or a pharmaceutically acceptable salt thereof.

In some embodiments, the compound is a compound of formula:

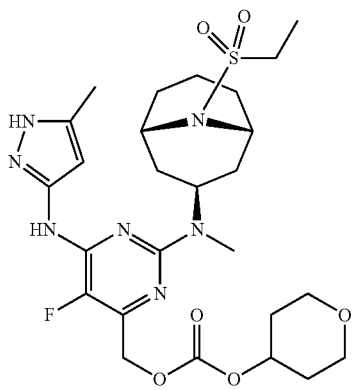

or a pharmaceutically acceptable salt thereof.

In some embodiments, the invention provides a pharmaceutical composition comprising a compound of the disclosure, or a pharmaceutically acceptable salt thereof, and a pharmaceutically-acceptable carrier. In some embodiments, the pharmaceutical composition further comprises one or more additional therapeutic agents. In some embodiments, the pharmaceutical composition is an ointment or a cream.

Chemical structures are named herein according to IUPAC conventions as implemented in ChemDraw software (PerkinElmer, Inc., Cambridge, Mass.). For example, compound 1:

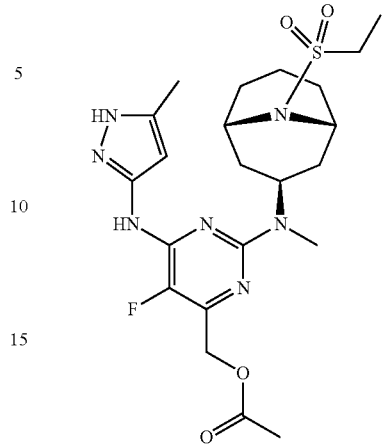

is designated as (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methyl acetate. The (1R,3s,5S) notation describes the exo orientation of the pyrimidinylamino group with respect to the 9-azabicyclo[3.3.1]nonane group.

Furthermore, the pyrazolyl moiety of compound (I) as well as other compounds disclosed herein exists in tautomeric form. It will be understood that although specific structures are shown, or named, in a particular form, the invention also includes the tautomer thereof.

The compounds of the disclosure contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

The compounds of formula (I) may exist as a free form or in various salt forms, such a mono-protonated salt form, a di-protonated salt form, a tri-protonated salt form, or mixtures thereof. All such forms are included within the scope of this invention, unless otherwise indicated.

This disclosure also includes isotopically-labeled versions of the compounds of the disclosure, including compounds of formula (I), where an atom has been replaced or enriched with an atom having the same atomic number but an atomic mass different from the atomic mass that predominates in nature. Examples of isotopes that may be incorporated into a compound of formula (I) include, but are not limited to, $^2$H, $^3$H, $^{11}$C, $^{13}$C, $^{14}$C, $^{13}$N, $^{15}$N, $^{15}$O, $^{17}$O, $^{18}$O, $^{35}$S, and $^{18}$F. Of particular interest are compounds of formula (I) enriched in tritium or carbon-14, which compounds can be used, for example, in tissue distribution studies. Also of particular interest are compounds of formula (I) enriched in deuterium especially at a site of metabolism, which compounds are expected to have greater metabolic stability. Additionally of particular interest are compounds of formula (I) enriched in a positron emitting isotope, such as $^{11}C$, $^{18}F$, $^{15}O$ and $^{13}N$ which compounds can be used, for example, in Positron Emission Tomography (PET) studies.

Definitions

When describing this invention including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like.

When a specific number of carbon atoms are intended for a particular term, the number of carbon atoms is shown preceding the term. For example, the term "$C_{1-3}$alkyl" means an alkyl group having from 1 to 3 carbon atoms wherein the carbon atoms are in any chemically-acceptable configuration, including linear or branched configurations.

The term "alkoxy" means the monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl, cyclopentyl, cyclohexyl, cycloheptyl, cyclooctyl, adamantyl, and the like.

The term "halogen" means fluoro, chloro, bromo or iodo.

The term "heterocyclyl", "heterocycle", "heterocyclic", or "heterocyclic ring" means a monovalent saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused or bridged). Representative heterocyclic groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbornanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, tetrahydropyran etc.

The term "therapeutically effective amount" means an amount sufficient to effect treatment when administered to a patient in need of treatment.

The term "treatment" as used herein means the treatment of a disease, disorder, or medical condition (such as a gastrointestinal inflammatory disease), in a patient, such as a mammal (particularly a human) which includes one or more of the following:

(a) preventing the disease, disorder, or medical condition from occurring, i.e., preventing the reoccurrence of the disease or medical condition or prophylactic treatment of a patient that is pre-disposed to the disease or medical condition;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like. For example, the cation can be a protonated form of a compound of formula (I), i.e. a form where one or more amino groups have been protonated by an acid. Typically, the salt is a pharmaceutically acceptable salt, although this is not required for salts of intermediate compounds that are not intended for administration to a patient.

General Synthetic Procedures

Compounds of formula (I), and intermediates thereof, can be prepared according to the following general methods and procedures using commercially-available or routinely-prepared starting materials and reagents. The substituents and variables (e.g., R, X, $R^a$ etc) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials known to those skilled in the art. In particular, it will be appreciated that compounds of formula (I) may be prepared by a variety of process routes in which reactants are combined in different orders to provide different intermediates en route to producing the final product.

General methods of preparing compounds of formula (I) are illustrated in scheme 1.

Scheme 1

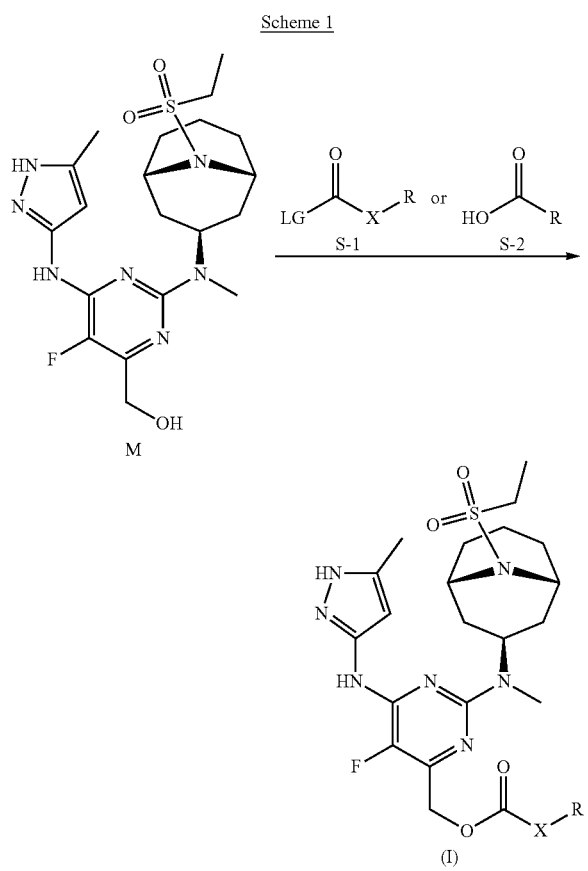

Compound M may be converted to a compound of formula (I) by reaction with S-1 in the presence of a base, where LG is a leaving group. In some embodiments, the leaving group is chloro and S-1 is either an acyl chloride or a chloroformate. In some embodiments, X is a bond and the reaction is conducted in the presence of DIPEA and DMAP. In some embodiments, X is O and the reaction is conducted in the presence of pyridine and either DMF or THF.

Alternatively, when X is a bond, compound M may be converted to a compound of formula (I) by coupling with a carboxylic acid S-2 in the presence of a coupling agent such as HATU. In some embodiments, the reaction is conducted in presence of DIPEA and DMAP.

Pharmaceutical Compositions

Compounds of formula (I) and pharmaceutically-acceptable salts thereof are typically used in the form of a pharmaceutical composition or formulation. Such pharmaceutical compositions may be administered to a patient by any acceptable route of administration including, but not limited to, oral, topical (including transdermal), rectal, nasal, inhaled, and parenteral modes of administration.

Accordingly, in one of its composition aspects, the invention is directed to a pharmaceutical composition comprising a pharmaceutically-acceptable carrier or excipient and a compound of formula (I), or a pharmaceutically-acceptable salt thereof. Optionally, such pharmaceutical compositions may contain other therapeutic and/or formulating agents if desired. When discussing compositions and uses thereof, the "compound of the invention" may also be referred to herein as the "active agent".

The pharmaceutical compositions of this disclosure typically contain a therapeutically effective amount of a compound of formula (I), or a pharmaceutically-acceptable salt thereof. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; including from about 5 to about 70% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture may then be shaped or loaded into tablets, capsules, pills and the like using conventional procedures and equipment.

The pharmaceutical compositions of this disclosure may be packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of this disclosure, or a pharmaceutically-acceptable salt thereof, as an active ingredient.

When intended for oral administration in a solid dosage form (i.e., as capsules, tablets, pills and the like), the pharmaceutical compositions of this disclosure will typically comprise the active agent, or a pharmaceutically acceptable salt thereof, and one or more pharmaceutically-acceptable carriers. Optionally, such solid dosage forms may comprise: fillers or extenders, such as starches, microcrystalline cellulose, lactose, dicalcium phosphate, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as crosscarmellose sodium, agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of this disclosure. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid, methacrylic acid ester copolymers, cellulose acetate trimellitate, carboxymethyl ethyl cellulose, hydroxypropyl methyl cellulose acetate succinate, and the like.

Pharmaceutical compositions of this disclosure may also be formulated to provide slow or controlled release of the active agent using, by way of example, hydroxypropyl methylcellulose in varying proportions; or other polymer matrices, liposomes and/or microspheres. In addition, the pharmaceutical compositions of this disclosure may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), oleic acid, glycerol, tetrahydrofuryl alcohol, polyethylene glycols and fatty acid esters of sorbitan, and mixtures thereof. Alternatively, certain liquid formulations can be converted, for example, by spray drying, to a powder, which is used to prepare solid dosage forms by conventional procedures.

Suspensions, in addition to the active ingredient, or a pharmaceutically acceptable salt thereof, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

A compound of formula (I), or a pharmaceutically-acceptable salt thereof, may also be administered parenterally (e.g. by intravenous, subcutaneous, intramuscular or intraperitoneal injection). For parenteral administration, the active agent, or a pharmaceutically acceptable salt thereof, is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more antioxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of this disclosure are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of this disclosure will typically comprise the active ingredient, or a pharmaceutically acceptable salt thereof, and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the disclosure, or a pharmaceutically-acceptable salt thereof, and a powder suitable for use in a powder inhaler. Suitable powder bases include, by way of example, lactose or starch.

Topical Formulations

To treat skin conditions, the compound of the disclosure, or a pharmaceutically-acceptable salt thereof, is preferably formulated for topical administration to the skin. Topical compositions comprise fluid or semi-solid vehicles that may include but are not limited to polymers, thickeners, buffers, neutralizers, chelating agents, preservatives, surfactants or emulsifiers, antioxidants, waxes or oils, emollients, sunscreens, and a solvent or mixed solvent system. The topical compositions useful in the subject invention can be made into a wide variety of product types. These include, but are not limited to lotions, creams, gels, sticks, sprays, ointments, pastes, foams, mousses, and cleansers. These product types can comprise several types of carrier systems including, but not limited to particles, nanoparticles, and liposomes. If desired, disintegrating agents can be added, such as the cross-linked polyvinyl pyrrolidone, agar or alginic acid or a salt thereof such as sodium alginate. Techniques for formulation and administration can be found in Remington: The Science and Practice of Pharmacy, 19th Ed. (Easton, Pa.: Mack Publishing Co., 1995). The formulation can be selected to maximize delivery to a desired target site in the body.

Lotions, which are preparations that are to be applied to the skin, or hair surface without friction, are typically liquid or semi-liquid preparations in which finely divided solid, waxy, or liquid are dispersed. Lotions will typically contain suspending agents to produce better dispersions as well as compounds useful for localizing and holding the active agent in contact with the skin or hair, e.g., methylcellulose, sodium carboxymethyl-cellulose, or the like.

Creams containing the active agent, or a pharmaceutically acceptable salt thereof, for delivery according to the present disclosure are viscous liquid or semisolid emulsions, either oil-in-water or water-in-oil. Cream bases are water-washable, and contain an oil phase, an emulsifier and an aqueous phase. The oil phase is generally comprised of petrolatum or a fatty alcohol, such as cetyl- or stearyl alcohol; the aqueous phase usually, although not necessarily, exceeds the oil phase in volume, and generally contains a humectant. The emulsifier in a cream formulation, as explained in Remington: The Science and Practice of Pharmacy, is generally a nonionic, anionic, cationic or amphoteric surfactant. Components of cream formulations may include: oil bases, such as petrolatrum, mineral oils, vegetable and animal oils, and triglycerides; cream bases, such as lanolin alcohols, stearic acid, and cetostearyl alcohol; a gel base, such as polyvinyl alcohol; solvents, such as, propylene glycol and polyethylene glycol; emulsifiers, such as polysorbates, stearates, such as glyceryl stearate, octylhydroxystearate, polyoxyl stearate, PEG stearyl ethers, isopropyl palmitate, and sorbitan monostearate; stabilizers, such as polysaccharides and sodium sulfite; emollients (i.e. moisturizers), such as medium chain triglycerides, isopropyl myristate, and dimethicone; stiffening agents, such as cetyl alcohol and stearyl alcohol; antimicrobial agents, such as methylparaben, propylparaben, phenoxyethanol, sorbic acid, diazolidinyl urea, and butylated hydroxyanisole; penetration enhancers, such as N-methylpyrrolidone, propylene glycol, polyethylene glycol monolaurate, and the like; and chelating agents, such as edetate disodium.

Gel formulations can also be used in connection with the present invention. As will be appreciated by those working in the field of topical drug formulation, gels are semisolid. Single-phase gels contain organic macromolecules distributed substantially uniformly throughout the carrier liquid, which is typically aqueous, but also may be a solvent or solvent blend.

Ointments, which are semisolid preparations, are typically based on petrolatum or other petroleum derivatives. As will be appreciated by the ordinarily skilled artisan, the specific ointment base to be used is one that provides for optimum delivery for the active agent chosen for a given formulation, and, preferably, provides for other desired characteristics as well, e.g., emolliency or the like. As with other carriers or vehicles, an ointment base should be inert, stable, nonirritating and non-sensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Water-soluble ointment bases may be prepared from polyethylene glycols of varying molecular weight; again, reference may be had to Remington: The Science and Practice of Pharmacy, supra, for further information. Suitable oily materials for use in ointment formulations include petrolatum (petroleum jelly), beeswax, cocoa butter, shea butter, and cetyl alcohol. Ointments may optionally additionally include penetration enhancers, if desired.

Useful formulations of this disclosure also encompass sprays. Sprays generally provide the active agent in an aqueous and/or alcoholic solution which can be misted onto the skin or hair for delivery. Such sprays include those formulated to provide for concentration of the active agent solution at the site of administration following delivery, e.g., the spray solution can be primarily composed of alcohol or other like volatile liquid in which the drug or active agent can be dissolved. Upon delivery to the skin or hair, the carrier evaporates, leaving concentrated active agent at the site of administration.

The topical pharmaceutical compositions may also comprise suitable solid or gel phase carriers. Examples of such carriers include but are not limited to calcium carbonate, calcium phosphate, various sugars, starches, cellulose derivatives, gelatin, and polymers such as polyethylene glycols.

The topical pharmaceutical compositions may also comprise a suitable emulsifier which refers to an agent that enhances or facilitates mixing and suspending oil-in-water or water-in-oil. The emulsifying agent used herein may consist of a single emulsifying agent or may be a nonionic, anionic, cationic or amphoteric surfactant or blend of two or more such surfactants; preferred for use herein are nonionic or anionic emulsifiers. Such surface-active agents are described in "McCutcheon's Detergent and Emulsifiers," North American Edition, 1980 Annual published by the McCutcheon Division, MC Publishing Company, 175 Rock Road, Glen Rock, N.J. 07452, USA.

High molecular weight alcohols may be used such as cetearyl alcohol, cetyl alcohol, stearyl alcohol, emulsifying wax, glyceryl monostearate. Other examples are ethylene glycol distearate, sorbitan tristearate, propylene glycol monostearate, sorbitan monooleate, sorbitan monostearate (SPAN 60), diethylene glycol monolaurate, sorbitan monopalmitate, sucrose dioleate, sucrose stearate (CRODESTA F-160), polyoxyethylene lauryl ether (BRIJ 30), polyoxyethylene (2) stearyl ether (BRIJ 72), polyoxyethylene (21) stearyl ether (BRIJ 721), polyoxyethylene monostearate (Myrj 45), polyoxyethylene sorbitan monostearate (TWEEN 60), polyoxyethylene sorbitan monooleate (TWEEN 80), polyoxyethylene sorbitan monolaurate (TWEEN 20) and sodium oleate. Cholesterol and cholesterol derivatives may also be employed in externally used emulsions.

Example of suitable nonionic emulsifying agents are described by Paul L. Lindner in "Emulsions and Emulsion", edited by Kenneth Lissant, published by Dekker, New York, N.Y., 1974. Examples of nonionic emulsifiers that may be used include but are not limited to BRIJ products such as BRIJ 2 (a polyoxyethylene (2) stearyl ether), BRIJ S20 (a polyoxyethylene (20) stearyl ether), BRIJ 72 (a polyoxyethylene (2) stearyl ether having an HLB of 4.9), BRIJ 721 (a polyoxyethylene (21) stearyl ether having an HLB of 15.5), Brij 30 (a polyoxyethylene lauryl ether having an HLB of 9.7), Polawax (emulsifying wax having an HLB of 8.0), Span 60 (sorbitan monostearate having an HLB of 4.7), Crodesta F-160 (sucrose stearate" having an HLB of 14.5).

The topical pharmaceutical compositions may also comprise suitable emollients. Emollients are materials used for the prevention or relief of dryness, as well as for the protection of the skin or hair. Useful emollients include, but are not limited to, cetyl alcohol, isopropyl myristate, stearyl alcohol, and the like. A wide variety of suitable emollients are known and can be used herein. See e.g., Sagarin, Cosmetics, Science and Technology, 2nd Edition, Vol. 1, pp. 32-43 (1972), and U.S. Pat. No. 4,919,934, to Deckner et al., issued Apr. 24, 1990, both of which are incorporated herein by reference in their entirety.

The topical pharmaceutical compositions may also comprise suitable antioxidants, substances known to inhibit oxidation. Antioxidants suitable for use in accordance with the present invention include, but are not limited to, butylated hydroxytoluene, ascorbic acid, sodium ascorbate, calcium ascorbate, ascorbic palmitate, butylated hydroxyanisole, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is butylated hydroxytoluene, butylated hydroxyanisole, propyl gallate, ascorbic acid, pharmaceutically acceptable salts or esters thereof, or mixtures thereof. Most preferably, the antioxidant is butylated hydroxytoluene.

The topical pharmaceutical compositions may also comprise suitable preservatives. Preservatives are compounds added to a pharmaceutical formulation to act as an antimicrobial agent. Among preservatives known in the art as being effective and acceptable in parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. See, e.g., Wallhausser, K.-H., Develop. Biol. Standard, 24:9-28 (1974) (S. Krager, Basel).

The topical pharmaceutical compositions may also comprise suitable chelating agents to form complexes with metal cations that do not cross a lipid bilayer. Examples of suitable chelating agents include ethylene diamine tetraacetic acid (EDTA), ethylene glycol-bis(beta-aminoethyl ether)-N,N,N',N'-tetraacetic acid (EGTA) and 8-amino-2-[(2-amino-5-methylphenoxy)methyl]-6-methoxyquinoline-N,N,N',N'-tetraacetic acid, tetrapotassium salt (QUIN-2). Preferably the chelating agents are EDTA and citric acid.

The topical pharmaceutical compositions may also comprise suitable neutralizing agents used to adjust the pH of the formulation to within a pharmaceutically acceptable range. Examples of neutralizing agents include but are not limited to trolamine, tromethamine, sodium hydroxide, hydrochloric acid, citric acid, and acetic acid.

The topical pharmaceutical compositions may also comprise suitable viscosity increasing agents. These components are diffusible compounds capable of increasing the viscosity of a polymer-containing solution through the interaction of the agent with the polymer. Carbopol Ultrez 10 may be used as a viscosity-increasing agent.

Liquid forms, such as lotions suitable for topical administration may include a suitable aqueous or non-aqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like. Additionally, the compounds can be delivered using a sustained-release system, such as semipermeable matrices of solid hydrophobic polymers containing the therapeutic agent. Various sustained-release materials have been established and are well known by those skilled in the art.

When formulated for topical application, a compound of formula (I), or a pharmaceutically-acceptable salt thereof, may be present at between 0.1 and 50% by weight. In some embodiments, a compound of formula (I), or a pharmaceutically-acceptable salt thereof, is present at between 0.1 and 25% by weight. In some embodiments, a compound of formula (I), or a pharmaceutically-acceptable salt thereof, is present at between 0.1 and 10% by weight. In some embodiments, a compound of formula (I), or a pharmaceutically-acceptable salt thereof, is present at between 0.25 and 5% by weight. In some embodiments, a compound of formula (I), or a pharmaceutically-acceptable salt thereof, is present at between 0.25 and 2% by weight. In some embodiments, a compound of formula (I), or a pharmaceutically-acceptable salt thereof, is present at between 0.25 and 1% by weight. In some embodiments, a compound of formula (I), or a pharmaceutically-acceptable salt thereof, is present at between 0.05 and 0.5% by weight. In some embodiments, a compound of formula (I), or a pharmaceutically-acceptable salt thereof, is present at about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.25, 3.5, 3.75, 4, 4.5, 5, 5.5, 6, 6.5, 7, 7.5, 8, 8.5, 9, 9.5 or 10% by weight.

In some embodiments, the pharmaceutical composition comprising a compound of formula (I), or a pharmaceutically-acceptable salt thereof, further comprises one or more additional therapeutic agents. In some embodiments, the one or more additional therapeutic agents is useful to treat an autoimmune skin disease. In some embodiments, the one or more additional therapeutic agents is useful to treat an inflammatory skin disease. In some embodiments, the one or more additional therapeutic agents is useful to treat atopic dermatitis. In some embodiments, the one or more additional therapeutic agents is useful to treat alopecia areata. Specific class of compounds or specific compounds that may be combined with a compound of formula (I) in a pharmaceutical composition are exemplified in later paragraphs.

The following non-limiting examples illustrate representative pharmaceutical compositions of the present invention.

Tablet Oral Solid Dosage Form

A compound of formula (I) or a pharmaceutically-acceptable salt thereof is dry blended with microcrystalline cellulose, polyvinyl pyrrolidone, and croscarmellose sodium in a ratio of 4:5:1:1 and compressed into tablets to provide a unit dosage of, for example, 5 mg, 20 mg or 40 mg active agent per tablet.

Capsule Oral Solid Dosage Form

A compound of formula (I) or a pharmaceutically-acceptable salt thereof is combined with microcrystalline cellulose, polyvinyl pyrrolidone, and croscarmellose sodium in a ratio of 4:5:1:1 by wet granulation and loaded into gelatin or hydroxypropyl methylcellulose capsules to provide a unit dosage of, for example, 5 mg, 20 mg or 40 mg active agent per capsule.

Liquid Formulation

A liquid formulation comprising a compound of formula (I) or a pharmaceutically-acceptable salt thereof (0.1%), water (98.9%) and ascorbic acid (1.0%) is formed by adding a compound of the disclosure, or a pharmaceutically-acceptable salt thereof, to a mixture of water and ascorbic acid.

Enteric Coated Oral Dosage Form

A compound of formula (I) or a pharmaceutically-acceptable salt thereof, is dissolved in an aqueous solution containing polyvinyl pyrrolidone and spray coated onto microcrystalline+cellulose or sugar beads in a ratio of 1:5 w/w active agent:beads and then an approximately 5% weight gain of an enteric coating comprising an acrylic copolymer, for example a combination of acrylic copolymers available under the trade names Eudragit-L® and Eudragit-S®, or hydroxypropyl methylcellulose acetate succinate is applied. The enteric coated beads are loaded into gelatin or hydroxypropyl methylcellulose capsules to provide a unit dosage of, for example, 30 mg active agent per capsule.

Enteric Coated Oral Dosage Form

An enteric coating comprising a combination of Eudragit-L® and Eudragit-S®, or hydroxypropyl methylcellulose acetate succinate is applied to a tablet oral dosage form or a capsule oral dosage form described above.

Ointment Formulation for Topical Administration

A compound of formula (I) or a pharmaceutically-acceptable salt thereof is combined with petrolatum, $C_8$-$C_{10}$ triglyceride, octylhydroxystearate, and N-methylpyrrolidone in a ratio to provide a composition containing 0.05% to 5% of active agent by weight.

Ointment Formulation for Topical Administration

A compound of formula (I) or a pharmaceutically-acceptable salt thereof is combined with petrolatum, $C_8$-$C_{10}$ triglyceride, octylhydroxystearate, benzyl alcohol and N-methylpyrrolidone in a ratio to provide a composition containing 0.05% to 5% of active agent by weight.

Ointment Formulation for Topical Administration

A compound of formula (I) or a pharmaceutically-acceptable salt thereof is combined with white petrolatum, propylene glycol, mono- and di-glycerides, paraffin, butylated hydroxytoluene, and edetate calcium disodium in a ratio to provide a composition containing 0.05% to 5% active agent by weight.

Ointment Formulation for Topical Administration

A compound of formula (I) or a pharmaceutically-acceptable salt thereof is combined with mineral oil, paraffin, propylene carbonate, white petrolatum and white wax to provide a composition containing 0.05% to 5% active agent by weight.

Cream Formulation for Topical Administration

Mineral oil is combined with a compound of formula (I) or a pharmaceutically-acceptable salt thereof, propylene glycol, isopropyl palmitate, polysorbate 60, cetyl alcohol, sorbitan monostearate, polyoxyl 40 stearate, sorbic acid, methylparaben and propylparaben to form an oil phase, which is combined with purified water by shear blending to provide a composition containing 0.05% to 5% active agent by weight.

Cream Formulation for Topical Administration

A cream formulation comprising a compound of formula (I) or a pharmaceutically-acceptable salt thereof, benzyl alcohol, cetyl alcohol, citric acid anhydrous, mono and di-glycerides, oleyl alcohol, propylene glycol, sodium cetostearyl sulphate, sodium hydroxide, stearyl alcohol, triglycerides, and water contains 0.05% to 5% active agent by weight.

Cream Formulation for Topical Administration

A cream formulation comprising a compound of formula (I) or a pharmaceutically-acceptable salt thereof, cetostearyl alcohol, isopropyl myristate, propylene glycol, cetomacrogol 1000, dimethicone 360, citric acid, sodium citrate, and purified water, with imidurea, methylparaben, and propylparaben, as preservatives, contains 0.05% to 5% active agent by weight.

Cream Formulation for Topical Administration

A cream formulation comprising a compound of formula (I) or a pharmaceutically-acceptable salt thereof, stearic acid, cetostearyl alcohol, isopropyl palmitate, octylhydroxystearate, BRIJ S2 (PEG 2 Stearyl Ether), BRIJ S20 (PEG 20 Stearyl Ether), N-Methylpyrrolidine, PEG and water contains 0.05% to 5% active agent by weight.

Cream Formulation for Topical Administration

A cream formulation comprising a compound of formula (I) or a pharmaceutically-acceptable salt thereof, stearic acid, cetostearyl alcohol, isopropyl palmitate, octylhydroxystearate, BRIJ S2 (PEG 2 Stearyl Ether), BRIJ S20 (PEG 20 Stearyl Ether), N-Methylpyrrolidine, PEG400 and water contains 0.05% to 5% active agent by weight.

Utility

Compounds of formula (I) have been shown to be potent inhibitors of the JAK family of enzymes: JAK1, JAK2, JAK3, and TYK2. Additionally, they have the ability to release an active metabolite. Inhibition of the family of JAK enzymes inhibits signaling of many key pro-inflammatory cytokines. Thus compounds of formula (I) are expected to be useful in the treatment of inflammatory diseases such as inflammatory and pruritic skin diseases, gastrointestinal inflammatory diseases inflammatory ocular diseases and inflammatory respiratory diseases.

Inflammatory Skin Disease

Atopic dermatitis has been associated with elevation of proinflammatory cytokines that rely on the JAK-STAT pathway, in particular, IL-4, IL-5, IL-10, IL-13, and IFNγ. Since compounds of formula (I) and their active metabolite exhibit potent inhibition at all four JAK enzymes, they are expected to potently inhibit the proinflammatory cytokines characteristic of atopic dermatitis and other inflammatory skin diseases. Compounds of formula (I) and their active metabolite were also shown here to exhibit high $pIC_{50}$ values for inhibition of IL-2 induced STAT5 phosphorylation in a cellular assay.

It is expected that sustained dermal levels of JAK inhibitors in the absence of significant systemic levels will result in potent local anti-inflammatory and anti-pruritic activity in the skin without systemically-driven adverse effects. Such compounds are expected to be beneficial in a number of dermal inflammatory or pruritic conditions that include, but are not limited to atopic dermatitis, vitiligo, non-segmental vitiligo, cutaneous T cell lymphoma and subtypes (Sezary syndrome, mycosis fungoides, pagetoid reticulosis, granulomatous slack skin, lymphomatoid papulosis, pityriasis lichenoides chronica, pityriasis lichenoides et varioliformis acuta, CD30+ cutaneous T-cell lymphoma, secondary cutaneous CD30+ large cell lymphoma, non-mycosis fungoides CD30− cutaneous large T-cell lymphoma, pleomorphic T-cell lymphoma, Lennert lymphoma, subcutaneous T-cell lymphoma, angiocentric lymphoma, blastic NK-cell lymphoma), prurigo nodularis, lichen planus, contact dermatitis, dyshidrotic eczema, eczema, nummular dermatitis, seborrheic dermatitis, stasis dermatitis, primary localized cutaneous amyloidosis, bullous pemphigoid, skin manifestations of graft versus host disease, pemphigoid, discoid lupus, granuloma annulare, lichen simplex chronicus, pruritus, vulvar/scrotal/perianal pruritus, lichen sclerosus, post herpetic neuralgia itch, lichen planopilaris, psoriasis, chronic hand eczema, hidradenitis suppurativa, hypereosinophilic syndrome, systemic lupus erythematosus, and folliculitis decalvans. In particular, atopic dermatitis (Bao et al., *JAK-STAT*, 2013, 2, e24137), alopecia areata (Xing et al., *Nat Med.* 2014, 20, 1043-1049) including subtypes such as alopecia areata monolocularis, alopecia areata multilocularis, ophiasis, alopecia areata universalis, alopecia areata totalis, and alopecia areata barbae, vitiligo (Craiglow et al, *JAMA Dermatol.* 2015, 151, 1110-1112), cutaneous T cell lymphoma (Netchiporouk et al., *Cell Cycle.* 2014; 13, 3331-3335), prurigo nodularis (Sonkoly et al., *J Allergy Clin Immunol.* 2006, 117, 411-417), lichen planus (Welz-Kubiak et al., *J Immunol Res.* 2015, ID:854747), primary localized cutaneous amyloidosis (Tanaka et al., *Br J Dermatol.* 2009, 161, 1217-1224), bullous pemphigoid (Feliciani et al., *Int J Immunopathol Pharmacol.* 1999, 12, 55-61), and dermal manifestations of graft versus host disease (Okiyama et al., *J Invest Dermatol.* 2014, 134, 992-1000) are characterized by elevation of certain cytokines that signal via JAK activation. Accordingly, compounds of formula (I) may be able to alleviate associated dermal inflammation or pruritus driven by these cytokines. In particular, compounds of formula (I), or a pharmaceutically acceptable salt thereof, are expected to be useful for the treatment of atopic dermatitis and other inflammatory skin diseases.

The compounds of formula (I) also possess advantageous solubility properties in aqueous and/or organic excipients which facilitate formulation into topical compositions.

The compounds of formula (I) also release an active metabolite, compound M, thereby increasing overall exposure to JAK inhibitors. Compound M possesses favorable properties including as a high clearance and permeability allowing for rapid systemic clearance and good skin permeability.

In some embodiments, therefore, the invention provides a method of treating an inflammatory or autoimmune skin disease in a mammal (e.g., a human), comprising applying a pharmaceutical composition comprising a compound of formula (I), or a pharmaceutically acceptable salt thereof, and a pharmaceutical carrier to the skin of the mammal.

In some embodiments, the invention provides a method of treating an inflammatory or autoimmune skin disease in a mammal (e.g., a human), comprising administering a compound of formula (I), or a pharmaceutically acceptable salt thereof, to the mammal. In some embodiments, the inflammatory skin disease is atopic dermatitis.

In some embodiments, the atopic dermatitis is mild to moderate. In some embodiments, the atopic dermatitis is moderate to severe. In some embodiments, the autoimmune skin disease is alopecia areata.

A compound of formula (I), or a pharmaceutically acceptable salt thereof, may also be used in combination with one or more compound useful to treat inflammatory skin diseases. In some embodiments, the one or more compound is a steroid, corticosteroid, antibiotic, Histamine H1 receptor antagonist, calcineurin inhibitor, IL-13 antagonist, PDE 4 inhibitor, G-protein coupled receptor-44 antagonist, IL-4 antagonist, 5-HT 1a receptor antagonist, 5-HT 2b receptor antagonist, Alpha 2 adrenoceptor agonist, cannabinoid CB1 receptor antagonist, CCR3 chemokine, antagonist, collagenase inhibitor, cytosolic phospholipase A2 inhibitor, eotaxin ligand inhibitor, GATA 3 transcription factor inhibitor, Histamine H4 receptor antagonist, IL-10 antagonist, IL-12 antagonist, IL-17 antagonist, IL-2 antagonist, IL-23 antagonist, IL-4 receptor modulator, IL-15 antagonist, IL-6 antagonist, IL-8 antagonist, IL-9 antagonist, IL-5 antagonist, immunoglobulin E antagonist, immunoglobulin E modulator, interferon gamma receptor antagonist, Interferon gamma ligand, Interleukin 33 ligand inhibitor, Interleukin-31 receptor antagonist, Leukotriene antagonist, Liver X receptor agonist, Liver X receptor beta agonist, nuclear factor kappa B inhibitor, OX-40 receptor antagonist, PGD2 antagonist, phospholipase A2 inhibitor, SH2 domain inositol phosphatase 1 stimulator, thymic stromal lymphoprotein ligand inhibitor, TLR modulator, TNF alpha ligand modulator, TLR9 gene stimulator, cytotoxic T-lymphocyte protein-4 stimulator, opioid receptor kappa agonist, galectin-3 inhibitor, histone deacetylase-1 inhibitor, histone deacetylase-2 inhibitor, histone deacetylase-3 inhibitor, histone deacetylase-6 inhibitor, histone deacetylase inhibitor, glucocorticoid agonist, Syk tyrosine kinase inhibitor, TrkA receptor antagonist, integrin alpha-4/beta-1 antagonist, Interleukin 1 like receptor antagonist, Interleukin-1 converting enzyme inhibitor, Interleukin-31 receptor antagonist, KCNA voltage-gated potassium channel-3 inhibitor, PDE4B gene inhibitor, Kallikrein 2 inhibitor, sphingosine-1-phosphate receptor-1 agonist, retinal pigment epithelium protein stimulator, T cell surface glycoprotein CD28 inhibitor, TGF beta antagonist, vanilloid VR1 antagonist, NK1 receptor antagonist, galectin-3 inhibitor, cytokine receptor antagonist, androgen receptor antagonist, sphingosine 1 phosphate phosphatase 1 stimulator, sphingosine-1-phosphate receptor-1 modulator, sphingosine-1-phosphate receptor-4 modulator, sphingosine-1-phosphate receptor-5 modulator, Interleukin-1 alpha ligand inhibitor, OX40 ligand inhibitor, Interleukin 1 like receptor 2 inhibitor, melanocyte stimulating hormone ligand, CD40 ligand receptor antagonist, osteopontin ligand modulator, Interleukin-1 beta ligand modulator, I-kappa B kinase beta inhibitor, 5-Alpha-reductase inhibitor, 5-Alpha-reductase-1 inhibitor; 5-Alpha-reductase-2 inhibitor, sodium channel inhibitor, NACHT LRR PYD domain protein 3 inhibitor, Wnt ligand modulator, Wnt 7A ligand, melanocortin MC1 receptor agonist, mTOR inhibitor, actin polymerization modulator, laminin-5 agonist, metalloprotease-2 modulator, metalloprotease-9 modulator, nuclear factor kappa B inhibitor, thymosin beta 4 ligand, thymosin receptor agonist, FGF-7 ligand, follistatin agonist, VEGF ligand, MEK-1 protein kinase inhibitor, Ras gene inhibitor, 5-Alpha-reductase inhibitor, alpha 1A adrenoceptor antagonist, Kallikrein 7 inhibitor, cytosolic phospholipase A2 inhibitor, elongation factor 2 inhibitor, NAD ADP ribosyltransferase stimulator, Interleukin-2 ligand, nuclear factor kappa B inhibitor, IL-22 antagonist, epidermal growth factor receptor agonist, retinal pigment epithelium protein stimulator, AMP activated protein kinase stimulator, ICE inhibitor, KCNA voltage-gated potassium channel-3 inhibitor, G-protein coupled bile acid receptor 1 agonist, or potassium channel modulator.

In some embodiments, a compound of formula (I), or a pharmaceutically acceptable salt thereof, is administered in combination with betamethasone, fucidic acid, GR-MD-02, dupilumab, rosiptor acetate, AS-101, ciclosporin, IMD-0354, secukinumab, Actimmune, lebrikizumab, CMP-001, mepolizumab, pegcantratinib, tezepelumab, MM-36, crisaborole, ALX-101, bertilimumab, FB-825, AX-1602, BNZ-1, abatacept, tacrolimus, ANB-020, JTE-052, ZPL-389, ustekinumab, GBR-830, GSK-3772847, ASN-002, remetinostat, apremilast, timapiprant, MOR-106, asivatrep, nemolizumab, fevipiprant, doxycycline, MDPK-67b, desloratadine, tralokinumab, fexofenadine, pimecrolimus, bepotastine, nalfurafine, VTP-38543, Q-301, ligelizumab, RVT-201, DMT-210, KPI-150, AKP-11, E-6005, AMG-0101, AVX-001, PG-102, ZPL-521, MEDI-9314, AM-1030, WOL-071007, MT-0814, betamethasone valerate, SB-011, epinastine, tacrolimus, tranilast, tradipitant, difamilast, LY-3375880, tapinarof, etokimab, clascoterone, etrasimod, bermekimab, KHK-4083, SAR-440340, BI-655130, EDP-1815, EDP-1066, DUR-928, afamelanotide, adriforant, diroleuton, FOL-005, KY-1005, PUR-0110, BTX-1204, ADSTEM, finasteride, BMX-010, BBI-5000, MSB-01, ATI-501, B-244, ASN-008, hypochlorous acid, diphenylcyclopropenone, RG-6149, LY-3454738, SB-414, S1P1 agonist, SM-04554, PL-8177, rapamycin, rose Bengal sodium, tonabacase, omiganan pentahydrochloride, desonide, allogeneic mesenchymal stem cell therapy, timbetasin, ASLAN-004, HSC-660, fluocinonide, niclosamide, antroquinonol, dutasteride, tamsulosin, UCA-001, dapsone, brilacidin, BPR-277, anapsos, dutasteride, denileukin diftitox, chanllergen, ARGX-112, PF-06817024, epinastine hydrochloride, IDP-124, nepidermin, roseomonas mucosa-based biotherapy, ENERGI-F701, HAT-1, lotamilast, HY-209, mometasone, melgain, doxycycline, TS-133, icomucret, CRTH2 antagonist, ACH-24, fluticasone propionate, CD-4802, minoxidil, finasteride, halometasone, tricomin, or viromed, or any combination thereof.

In some embodiments, a compound of formula (I), or a pharmaceutically acceptable salt thereof, is administered in combination with a steroid, an antibiotic and a moisturizer (Lakhani et al., *Pediatric Dermatology*, 2017, 34, 3, 322-325). In some embodiments, the one or more compound is a gram positive antibiotic, such as mupirocin or fusidic acid.

A compound of formula (I), or a pharmaceutically-acceptable salt thereof, may also be used in combination with gram positive antibiotics, such as mupirocin and fusidic acid, to treat inflammatory skin disease. In one aspect, therefore, the invention provides a method of treating an inflammatory skin disease in a mammal, the method comprising applying a compound of the disclosure, or a pharmaceutically-acceptable salt thereof, and a gram positive antibiotic to the skin of the mammal. In another aspect, the invention provides a pharmaceutical composition comprising a compound of the disclosure, or a pharmaceutically-acceptable salt thereof, a gram positive antibiotic, and a pharmaceutically-acceptable carrier.

In another aspect, therefore, the invention provides a therapeutic combination for use in the treatment of skin inflammatory disorders, the combination comprising a compound of formula (I), or a pharmaceutically acceptable salt thereof and one or more other therapeutic agents useful for treating skin inflammatory disorders. Secondary agent(s), when included, are present in a therapeutically effective amount, i.e. in any amount that produces a therapeutically beneficial effect when co-administered with a compound of formula (I), or a pharmaceutically-acceptable salt thereof.

Also provided, therefore, is a pharmaceutical composition comprising a compound of formula (I), or a pharmaceutically salt thereof and one or more other therapeutic agents useful for treating skin inflammatory disorders.

Further, in a method aspect, the invention provides a method of treating skin inflammatory disorders, the method comprising administering to the mammal a compound of formula (I), or a pharmaceutically acceptable salt thereof, and one or more other therapeutic agents useful for treating skin inflammatory disorders.

Gastrointestinal Inflammatory Disease

Due to its inhibition of the JAK family of enzymes, compounds of formula (I) are expected to be useful for a variety of gastrointestinal inflammatory indications that include, but are not limited to, ulcerative colitis (proctosigmoiditis, pancolitis, ulcerative proctitis and left-sided colitis), Crohn's disease, collagenous colitis, lymphocytic colitis, Behcet's disease, celiac disease, immune checkpoint inhibitor induced colitis, ileitis, eosinophilic esophagitis, graft versus host disease-related colitis, and infectious colitis. Ulcerative colitis (Reimund et al., *J Clin Immunology*, 1996, 16, 144-150), Crohn's disease (Woywodt et al., *Eur J Gastroenterology Hepatology*, 1999, 11, 267-276), collagenous colitis (Kumawat et al., *Mol Immunology*, 2013, 55, 355-364), lymphocytic colitis (Kumawat et al., 2013), eosinophilic esophagitis (Weinbrand-Goichberg et al., *Immunol Res*, 2013, 56, 249-260), graft versus host disease-related colitis (Coghill et al., *Blood*, 2001, 117, 3268-3276), infectious colitis (Stallmach et al., *Int J Colorectal Dis*, 2004, 19, 308-315), Behcet's disease (Zhou et al., *Autoimmun Rev*, 2012, 11, 699-704), celiac disease (de Nitto et al., *World J Gastroenterol*, 2009, 15, 4609-4614), immune checkpoint inhibitor induced colitis (e.g., CTLA-4 inhibitor-induced colitis; (Yano et al., *J Translation Med*, 2014, 12, 191), PD-1- or PD-L1-inhibitor-induced colitis), and ileitis (Yamamoto et al., *Dig Liver Dis*, 2008, 40, 253-259) are characterized by elevation of certain pro-inflammatory cytokine levels. As many pro-inflammatory cytokines signal via JAK activation, compounds described in this application may be able to alleviate the inflammation and provide symptom relief.

In some embodiments, therefore, the disclosure provides a method of treating a gastrointestinal inflammatory disease in a mammal (e.g., a human), comprising administering to the mammal a pharmaceutical composition comprising a pharmaceutically-acceptable carrier and a compound of formula (I) or a pharmaceutically-acceptable salt thereof.

In some embodiments, the disclosure provides a method of treating a gastrointestinal inflammatory disease in a mammal (e.g., a human), comprising administering to the mammal a compound of formula (I), or a pharmaceutically acceptable salt thereof.

The disclosure further provides a method of treating ulcerative colitis in a mammal, the method comprising administering to the mammal a compound of the disclosure, or a pharmaceutically-acceptable salt thereof, or a pharmaceutical composition comprising a pharmaceutically-acceptable carrier and a compound of the disclosure, or a pharmaceutically-acceptable salt thereof.

When used to treat ulcerative colitis, the compound of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating ulcerative colitis and other gastrointestinal inflammatory disorders are expected to range from about 1 to about 400 mg/day of active agent, including from about 5 to about 300 mg/day and from about 20 to about 70 mg per day of active agent for an average 70 kg human.

Compounds of formula (I), or a pharmaceutically-acceptable salt thereof, may also be used in combination with one or more agents which act by the same mechanism or by different mechanisms to effect treatment of gastrointestinal inflammatory disorders. Useful classes of agents for combination therapy include, but are not limited to, aminosalicylates, steroids, systemic immunosuppressants, anti-TNFα antibodies, anti-VLA-4 antibodies, anti-integrin $\alpha_4\beta_7$ antibodies, anti-bacterial agents, and anti-diarrheal medicines.

Aminosalicylates that may be used in combination with a compound of formula (I), include, but are not limited to, mesalamine, osalazine and sulfasalazine. Examples of steroids include, but are not limited to, prednisone, prednisolone, hydrocortisone, budesonide, beclomethasone, and fluticasone. Systemic immunosuppressants useful for treatment of inflammatory disorders include, but are not limited to cyclosporine, azathioprine, methotrexate, 6-mercaptopurine, and tacrolimus. Further, anti-TNFα antibodies, which include, but are not limited to, infliximab, adalimumab, golimumab, and certolizumab, may be used in combination therapy. Useful compounds acting by other mechanisms include anti-VLA-4 antibodies, such as natalizumab, anti-integrin $α_4β_7$ antibodies, such as vedolizumab, anti-bacterial agents, such as rifaximin, and anti-diarrheal medicines, such as loperamide. (Mozaffari et al. *Expert Opin. Biol. Ther.* 2014, 14, 583-600; Danese, *Gut,* 2012, 61, 918-932; Lam et al., *Immunotherapy,* 2014, 6, 963-971).

In another aspect, therefore, the disclosure provides a therapeutic combination for use in the treatment of gastrointestinal inflammatory disorders, the combination comprising a compound of the disclosure, or a pharmaceutically-acceptable salt thereof, and one or more other therapeutic agents useful for treating gastrointestinal inflammatory disorders. For example, the disclosure provides a combination comprising a compound of the disclosure, or a pharmaceutically-acceptable salt thereof, and one or more agents selected from aminosalicylates, steroids, systemic immunosuppressants, anti-TNFα antibodies, anti-VLA-4 antibodies, anti-integrin $α_4β_7$ antibodies, anti-bacterial agents, and anti-diarrheal medicines. Secondary agent(s), when included, are present in a therapeutically effective amount, i.e. in any amount that produces a therapeutically beneficial effect when co-administered with a compound of the disclosure, or a pharmaceutically-acceptable salt thereof.

Also provided, therefore, is a pharmaceutical composition comprising a compound of formula (I), or a pharmaceutically-acceptable salt thereof, and one or more other therapeutic agents useful for treating gastrointestinal inflammatory disorders.

Further, in a method aspect, the disclosure provides a method of treating gastrointestinal inflammatory disorders, the method comprising administering to the mammal a compound of formula (I), or a pharmaceutically acceptable salt thereof, and one or more other therapeutic agents useful for treating gastrointestinal inflammatory disorders.

Respiratory Diseases

Cytokines which signal through the JAK-STAT pathway, in particular IL-2, IL-3, IL-4, IL-5, IL-6, IL-9, IL-11, IL-13, IL-23, IL-31, IL-27, thymic stromal lymphopoietin (TSLP), interferon-γ (IFNγ) and granulocyte-macrophage colony-stimulating factor (GM-CSF) have been implicated in asthma inflammation and in other inflammatory respiratory diseases. As described above, compounds of formula (I) have been shown to be a potent inhibitor of Janus kinases and has demonstrated potent inhibition of IL-13 pro-inflammatory cytokines in cellular assays.

The anti-inflammatory activity of JAK inhibitors has been robustly demonstrated in preclinical models of asthma (Malaviya et al., *Int Immunopharmacol,* 2010, 10, 829,-836; Matsunaga et al., *Biochem and Biophys Res Commun,* 2011, 404, 261-267; Kudlacz et al., *Eur J Pharmacol,* 2008, 582, 154-161.) Accordingly, compounds of formula (I), or a pharmaceutically acceptable salt thereof, are expected to be useful for the treatment of inflammatory respiratory disorders such as asthma. Inflammation and fibrosis of the lung is characteristic of other respiratory diseases in addition to asthma such as chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, and bronchiolitis obliterans. Compounds of formula (I), or a pharmaceutically acceptable salt thereof, therefore, may be useful for the treatment of chronic obstructive pulmonary disease, cystic fibrosis, pneumonitis, interstitial lung diseases (including idiopathic pulmonary fibrosis), acute lung injury, acute respiratory distress syndrome, bronchitis, emphysema, bronchiolitis obliterans, chronic lung allograft dysfunction (CLAD), lung transplant rejections, and sarcoidosis.

In one aspect, therefore, the disclosure provides a method of treating a respiratory disease in a mammal (e.g., a human) comprising administering to the mammal a compound of formula (I), or a pharmaceutically-acceptable salt thereof.

In one aspect, the respiratory disease is asthma, chronic obstructive pulmonary disease, cystic fibrosis, pneumonitis, chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, bronchiolitis obliterans, allergic rhinitis or sarcoidosis. In another aspect, the respiratory disease is asthma or chronic obstructive pulmonary disease.

In a further aspect, the respiratory disease is a lung infection, a helminthic infection, pulmonary arterial hypertension, sarcoidosis, lymphangioleiomyomatosis, bronchiectasis, or an infiltrative pulmonary disease. In yet another aspect, the respiratory disease is drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Loffler syndrome, bronchiolitis obliterans organizing pneumonia, or immune-checkpoint-inhibitor induced pneumonitis.

The disclosure further provides a method of treating a respiratory disease, the method comprising administering to the mammal a pharmaceutical composition comprising a compound of formula (I), or a pharmaceutically-acceptable salt thereof and a pharmaceutically-acceptable carrier.

Compounds of formula (I), or a pharmaceutically acceptable salt thereof, may also be used in combination with one or more compound useful to respiratory diseases.

Ocular Diseases

Many ocular diseases have been associated with elevations of proinflammatory cytokines that rely on the JAK-STAT pathway.

Compounds of formula (I), or a pharmaceutically acceptable salt thereof, therefore, may be useful for the treatment of a number of ocular diseases that include, but are not limited to, uveitis, diabetic retinopathy, diabetic macular edema, dry eye disease, age-related macular degeneration, and atopic keratoconjunctivitis.

In particular, uveitis (Horai and Caspi, *J Interferon Cytokine Res,* 2011, 31, 733-744), diabetic retinopathy (Abcouwer, *J Clin Cell Immunol,* 2013, Suppl 1, 1-12), diabetic macular edema (Sohn et al., *American Journal of Opthamology,* 2011, 152, 686-694), dry eye disease (Stevenson et al, *Arch Ophthalmol,* 2012, 130, 90-100), retinal vein occlusion (Shchuko et al, *Indian Journal of Ophthalmology,* 2015, 63(12), 905-911), and age-related macular degeneration (Knickelbein et al, *Int Ophthalmol Clin,* 2015, 55(3), 63-78) are characterized by elevation of certain pro-inflammatory cytokines that signal via the JAK-STAT pathway. Accordingly, compounds of formula (I), or a pharmaceutically acceptable salt thereof, may be able to alleviate the associated ocular inflammation and reverse disease progression or provide symptom relief.

In one aspect, therefore, the disclosure provides a method of treating an ocular disease in a mammal comprising administering a compound of formula (I), or a pharmaceutically-acceptable salt thereof or a pharmaceutical composition comprising a compound of formula (I), or a pharmaceutically-acceptable salt thereof and a pharmaceutical carrier to the eye of the mammal. In one aspect, the ocular disease is uveitis, diabetic retinopathy, diabetic macular edema, dry eye disease, age-related macular degeneration, or atopic keratoconjunctivitis. In one aspect, the method comprises administering a compound of formula (I), or a pharmaceutically acceptable salt thereof by intravitreal injection.

Compounds of formula (I), or a pharmaceutically acceptable salt thereof, may also be used in combination with one or more compound useful to ocular diseases.

Other Diseases

Compounds of formula (I), or a pharmaceutically acceptable salt thereof, may also be useful to treat other diseases such as other inflammatory diseases, autoimmune diseases or cancers.

Compounds of formula (I), or a pharmaceutically acceptable salt thereof, may be useful to treat oral cavities, oral mucositis and recurrent aphthous stomatitis.

Compounds of formula (I), or a pharmaceutically acceptable salt thereof, may be useful to treat one or more of arthritis, rheumatoid arthritis, juvenile rheumatoid arthritis, transplant rejection, xerophthalmia, psoriatic arthritis, diabetes, insulin dependent diabetes, motor neurone disease, myelodysplastic syndrome, pain, sarcopenia, cachexia, septic shock, systemic lupus erythematosus, leukemia, chronic lymphocytic leukemia, chronic myelocytic leukemia, acute lymphoblastic leukemia, acute myelogenous leukemia, ankylosing spondylitis, myelofibrosis, B-cell lymphoma, hepatocellular carcinoma, Hodgkins disease, breast cancer, Multiple myeloma, melanoma, squamous cell carcinoma, non-Hodgkin lymphoma, non-small-cell lung cancer, ovarian clear cell carcinoma, ovary tumor, pancreas tumor, polycythemia vera, Sjoegrens syndrome, soft tissue sarcoma, sarcoma, splenomegaly, T-cell lymphoma, and thalassemia major.

The disclosure, thereof, provides a method of treating these diseases in a mammal comprising administering a compound of formula (I), or a pharmaceutically-acceptable salt thereof or a pharmaceutical composition comprising a compound of formula (I), or a pharmaceutically-acceptable salt thereof and a pharmaceutical carrier to the mammal.

In the previous paragraphs, when used in combination therapy, the agents may be formulated in a single pharmaceutical composition, as disclosed above, or the agents may be provided in separate compositions that are administered simultaneously or at separate times, by the same or by different routes of administration. When administered separately, the agents are administered sufficiently close in time so as to provide a desired therapeutic effect. Such compositions can be packaged separately or may be packaged together as a kit. The two or more therapeutic agents in the kit may be administered by the same route of administration or by different routes of administration.

Examples

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
Bn=benzyl
Boc=tert-Butyloxycarbonyl
d=day(s)
DIPEA=N,N-diisopropylethylamine
DMF=N,N-dimethylformamide
DMSO=dimethyl sulfoxide
EtOAc=ethyl acetate
EtOH=ethyl alcohol
h=hour(s)
HATU=N,N,N',N'-tetramethyl-O-(7-azabenzotriazol-1-yl)uronium hexafluorophosphate
IPA=isopropyl alcohol
MeOH=methanol
min=minute(s)
NMP=N-methylpyrrolidone
RT=room temperature
TEA=triethylamine
THF=tetrahydrofuran
TFA=trifluoroacetic acid Reagents and solvents were purchased from commercial suppliers (Aldrich, Fluka, Sigma, etc.), and used without further purification. Progress of reaction mixtures was monitored by thin layer chromatography (TLC), analytical high performance liquid chromatography (anal. HPLC), and/or mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as $CD_3OD$, $CDCl_3$, or $d_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or a Waters (Milford, Mass.) 3100 instrument, coupled to autopurification systems.

Unless otherwise indicated the following conditions were used for preparative HPLC purifications.

Column: C18, 5 μm 21.2×150 mm or C18, 5 μm 21×250 mm or
C14, 5 μm 21×150 mm
Column temperature: Room Temperature
Flow rate: 20.0 mL/min
Mobile Phases: A=Water+0.05% TFA
B=ACN+0.05% TFA,
Injection volume: (100-1500 μL)
Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 1004 injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Analytic HPLC Conditions

Method a
Column: LUNA C18 (2), 150×4.60 mm, 3 µm
Column temperature: 37° C.
Flow rate: 1.0 mL/min
Injection volume: 5 µL
Sample preparation: Dissolve in 1:1 ACN:water
Mobile Phases: A=Water:ACN:TFA (98:2:0.05)
B=Water:ACN:TFA (2:98:0.05)
Detector wavelength: 250 nm
Gradient: 32 min total (time (min)/% B): 0/2, 10/20, 24/90, 29/90, 30/2, 32/2

Method B
Column: LUNA C18 (2), 150×4.60 mm, 3 µm
Column temperature: 37° C.
Flow rate: 1.0 mL/min
Injection volume: 10 µL
Sample preparation: Dissolve in 1:1 ACN:water
Mobile Phases: A=Water:ACN:TFA (98:2:0.05)
B=Water:ACN:TFA (10:90:0.05)
Detector wavelength: 254 nm
Gradient: 35 min total (time (min)/% B): 0/2, 20/25, 23/90, 26/90, 27/2, 35/2

Method C
Column: Poroshell 120 SB-Aq, 150 mm by 4.6 mm, 2.7 micron part #683975-914
Column temperature: 35° C.
Flow rate: 1.0 mL/min
Injection volume: 5 µL
Sample preparation: Dissolve in 50:MPB:50 MPA
Mobile Phases: A=Acetonitrile:Water:Trifluoroacetic acid (1:99:0.20)
B=Acetonitrile:Water:Trifluoroacetic acid (90:10:0.20)
Gradient:

| Time, min | % A | % B |
|---|---|---|
| 0.0 | 98.0 | 2.0 |
| 16.0 | 40.0 | 60.0 |
| 22.0 | 0.0 | 100.0 |
| 25.0 | 0.0 | 100.0 |
| 25.1 | 98.0 | 2.0 |
| 30.0 | 98.0 | 2.0 |

Preparation 1: tert-butyl ((1R,3s,5S)-9-(ethylsulfonyl)-9-azabicyclo[3.3.1]nonan-3-yl)(methyl)carbamate

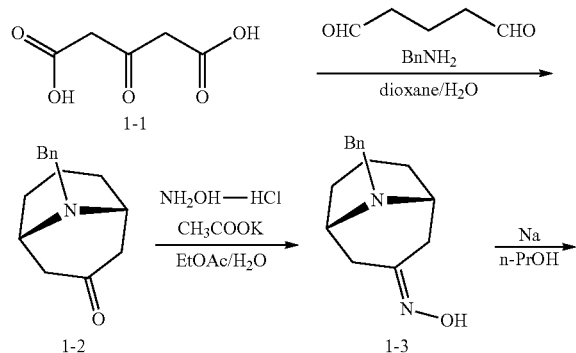

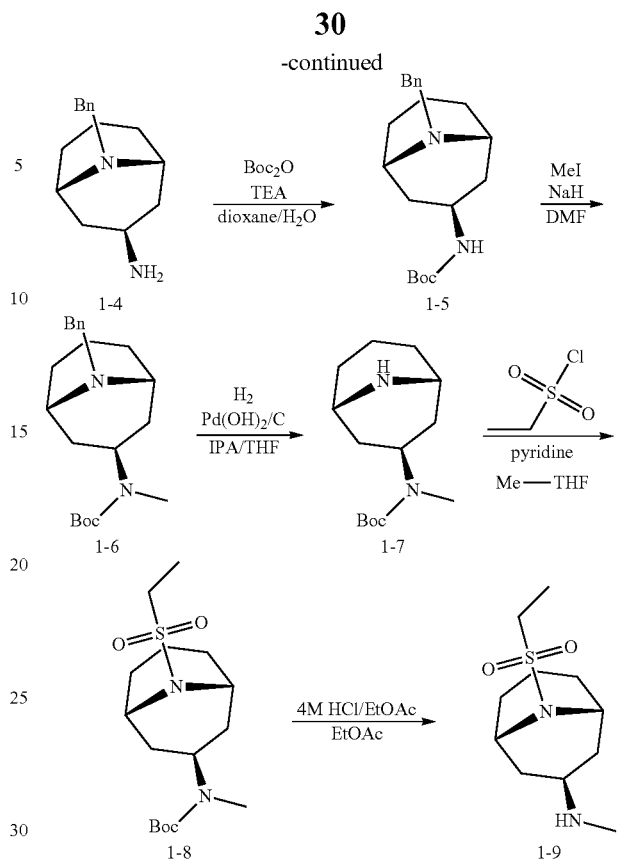

Step 1: Five reactions were carried out in parallel. To a solution of compound 1-1 (2.00 kg, 13.7 mol, 1.00 eq) in dioxane (5.00 L) and water (20.0 L) was added glutaraldehyde (2.06 kg, 20.5 mol, 1.5 eq) and phenylmethanamine (1.54 kg, 14.4 mol, 1.05 eq) drop-wise at 10° C. After addition, the reaction mixture was stirred at 20° C. for 16 h. TLC (petroleum ether:ethyl acetate=5:1, product $R_f$=0.40) and LCMS indicated the reaction was complete. The pH value of the reaction mixture was adjusted to 2 with concentrated HCl (12 N) at 20° C. After addition, the reaction mixture was heated to 60° C. and stirred for 1 h. After cooling to 10° C., ethyl acetate (10.0 L) was added to the mixture. Then the pH value of the mixture was adjusted to 10 by adding an aqueous solution of sodium hydroxide (12 N) at 10° C. The mixture was stirred for 10 min. The organic layer was separated. The aqueous layer was extracted with ethyl acetate (3.00 L). The combined organic layers were washed with brine (4.00 L), dried over sodium sulfate, and filtered. The organic layer for the five parallel reactions was combined and concentrated. The residue was purified by column chromatography (SiO$_2$, petroleum ether:ethyl acetate=30: 1-2:1) to give compound 1-2 (10.0 kg, 51.5% yield, 97% purity). (m/z): [M+H]$^+$ calcd for C$_{15}$H$_{19}$NO 230.15 found 230.0. $^1$H NMR: 400 MHz DMSO-d$_6$ δ 7.24-7.41 (m, 5H), 3.88 (s, 2H), 3.20-3.21 (m, 2H), 2.73-2.79 (m, 2H), 2.07 (d, J=16.4 Hz, 2H), 1.75-1.84 (m, 2H), 1.45-1.50 (m, 3H), 1.24-1.36 (m, 1H).

Step 2: Three reactions were carried out in parallel. To a solution of compound 1-2 (3.00 kg, 13.1 mol, 1.0 eq) in ethyl acetate (24.0 L) and water (9.00 L) was added CH$_3$COOK (2.05 kg, 20.9 mol, 1.6 eq) and NH$_2$OH—HCl (1.82 kg, 26.2 mol, 2.0 eq) at 20° C. The suspension was heated to 45° C. and stirred for 16 h. TLC (petroleum ether: ethyl acetate=2: 1, product $R_f$=0.30) and LCMS indicated the reaction was complete. The pH value of the suspension was adjusted to 8 with saturated sodium bicarbonate solution, then diluted with water (15.0 L) and ethyl acetate (10.0 L). The organic layer was separated. The aqueous layer was extracted with ethyl acetate (10.0 L×3). The organic layer of the three reactions was combined, dried over sodium sulfate, filtered and concentrated. The crude product was diluted with n-heptane (12.0 L), and stirred for 12 h. The solid was collected by filtration to give compound 1-3 (8.00 kg, 83.4% yield). (m/z): [M+H]$^+$ calcd for $C_{15}H_{20}N_2O$ 245.16 found 245.1. $^1$H NMR: 400 MHz DMSO-$d_6$ 10.16 (s, 1H), 7.22-7.38 (m, 5H), 3.83 (s, 2H), 2.97 (br s, 2H), 2.87 (d, J=16.0 Hz, 1H), 2.60-2.62 (m, 1H), 2.20-2.25 (m, 1H), 2.09-2.13 (m, 1H), 1.72-1.85 (m, 3H), 1.39-1.49 (m, 3H).

Step 4: Forty-five reactions were carried out in parallel. To a solution of compound 1-3 (160 g, 655 mmol, 1.0 eq) in n-PrOH (3.20 L) at 110° C. was added Na (181 g, 7.86 mol, 12 eq) in portions over 3 h. The mixture was stirred at 110° C. for 2 h. TLC (petroleum ether:ethyl acetate=2:1, SM $R_f$=0.40) indicated the reaction was complete. The mixture was cooled to 70° C., poured into ice water (4.00 L). The aqueous layer was extracted with ethyl acetate (1.00 L×2). The combined organic layer of the forty-five reactions was washed with brine (20.0 L), dried over sodium sulfate, filtered and concentrated. The residue was diluted with n-hexane (12.0 L), stirred for 12 h. The suspension was filtered to get filtrate. The filtrate was concentrated to give compound 1-4 (6.00 kg, 88.4% yield) as a yellow oil. $^1$H NMR 400 MHz DMSO-$d_6$: δ 7.18-7.35 (m, 5H), 3.76 (s, 2H), 3.26-3.35 (m, 1H), 2.76 (s, 2H), 1.86-1.90 (m, 2H), 1.67-1.73 (m, 2H), 1.54-1.59 (m, 5H), 1.41-1.45 (m, 3H).

Step 5: Two reactions were carried out in parallel. To a solution of compound 1-4 (2.10 kg, 9.12 mol, 1.1 eq) in dioxane (12.6 L) and water (1.26 L) was added Et$_3$N (1.01 kg, 10.0 mol, 1.1 eq) and (Boc)$_2$O (2.19 kg, 10.0 mol, 1.1 eq) drop-wise at 0° C., with the temperature below 20° C. The mixture was heated to 40° C. and stirred for 10 h. TLC (petroleum ether:ethyl acetate=2:1, product $R_f$=0.40) showed the reaction was complete. The mixture was cooled to 10° C., filtered to get filter cake. The filtrate was concentrated. The filter cake was washed with n-hexane (3.00 L) to give compound 1-5 (4.00 kg, 66.4% yield) as a white solid. $^1$H NMR: 400 MHz DMSO-$d_6$: δ 7.28-7.33 (m, 4H), 7.19-7.22 (m, 1H), 6.64 (d, J=8.0 Hz, 1H), 4.10-4.17 (m, 1H), 3.77 (s, 2H), 2.77 (s, 2H), 1.88-1.90 (m, 2H), 1.72-1.75 (m, 3H), 1.57-1.61 (m, 3H), 1.43-1.48 (m, 2H), 1.38 (s, 9H).

Step 6: Four reactions were carried out in parallel. To a suspension of compound 1-5 (1.50 kg, 4.54 mol, 1.0 eq) in DMF (13.5 L) was added NaH (272 g, 6.81 mol, 60% purity, 1.5 eq) portion-wise at 0° C. under N$_2$. The suspension was naturally warmed to 25° C. and stirred for 30 min. After it was cooled down to 0° C., MeI (773 g, 5.45 mol, 1.2 eq) was added drop-wise to the suspension. The reaction mixture was naturally warmed to 25° C. and stirred for 12 h. TLC (petroleum ether:ethyl acetate=5:1, product $R_f$=0.50) and LCMS showed the reaction was complete. The mixture was poured into ice water (30.0 L), extracted with ethyl acetate (9.00 L, 3.00 L). The combined organic layer of the four reactions was washed with ice water (20.0 L), brine (10.0 L), dried over sodium sulfate, filtered and concentrated to give compound 1-6 (6.00 kg, crude) as a yellow oil. The crude product was used for the next step. $^1$H NMR: 400 MHz DMSO-$d_6$ δ 7.21-7.37 (m, 5H), 4.87 (br s, 1H), 3.80 (s, 2H), 2.86 (s, 2H), 2.68 (s, 3H), 1.64-1.99 (m, 6H), 1.40-1.49 (m, 13H). (m/z): [M+H]$^+$ calcd for $C_{21}H_{32}N_2O_2$ 344.25 found 345.2.

Step 7: Thirty-nine reactions were carried out in parallel. To a solution of compound 1-6 (150 g, 435 mmol, 1.0 eq) in IPA (500 mL) and THF (500 mL) was added Pd(OH)$_2$/C (70 g, 40% purity). The suspension was degassed under vacuum and purged with H$_2$ several times. The mixture was stirred under H$_2$ (50 psi) at 25° C. for 16 h. TLC (petroleum ether:ethyl acetate=5:1, SM $R_f$=0.50) and LCMS indicated the reaction was complete. The thirty-nine reactions were combined. The mixture was filtered to get filtrate. The filter cake was washed with IPA/THF (1:1, 25.0 L). The combined filtrate was concentrated to give compound 1-7 (3.85 kg, crude) as a light yellow oil. The crude product was used for the next step directly. (m/z): [M+H]$^+$ calcd for $C_{14}H_{26}N_2O_2$ 255.20 found 255.1. $^1$H NMR: 400 MHz DMSO-$d_6$ δ 4.88 (br s, 1H), 3.08 (s, 2H), 2.60 (s, 3H), 1.73-1.76 (m, 5H), 1.51-1.61 (m, 5H), 1.39 (s, 9H).

Step 8: Four reactions were carried out in parallel. To a solution of compound 1-7 (750 g, 2.95 mol, 1.0 eq) in 2-methyl tetrahydrofuran (3.00 L) was added pyridine (466 g, 5.90 mol, 2.0 eq) and ethanesulfonyl chloride (398 g, 3.10 mol, 1.05 eq) drop-wise at 0° C. under N$_2$. The mixture was warmed to 25° C. and stirred for 3 h. TLC (petroleum ether:ethyl acetate=2:1, product $R_f$=0.50) indicated the reaction was complete. The four reactions were combined. The mixture was quenched with ice water (10.0 L). The organic layer was separated, washed with 0.5 N HCl (3.00 L×2). The combined aqueous layer was extracted with ethyl acetate (3.00 L), the organic layer was washed with 0.5 N HCl (500 mL) again. The combined organic layer was washed with brine (5.00 L), dried over sodium sulfate, filtered and concentrated to give compound 1-8 (2.20 kg, crude) as a yellow oil. The crude product was used in the next step. $^1$H NMR: 400 MHz DMSO-$d_6$ δ 4.94 (br s, 1H), 3.98 (s, 2H), 3.10 (q, J=7.2 Hz, 2H), 2.58 (s, 3H), 1.83-1.91 (m, 5H), 1.56-1.71 (m, 5H), 1.40 (s, 9H), 1.19 (t, J=7.2 Hz, 3H).

Step 9: Four reactions were carried out in parallel. To a solution of compound 1-8 (550 g, 1.59 mol, 1.0 eq) in EtOAc (2.75 L) was added HCl/EtOAc (4 M, 3.0 eq) drop-wise at 25° C. The mixture was stirred at 25° C. for 12 h. TLC (petroleum ether:ethyl acetate=2:1, SM $R_f$=0.50) showed the reaction was complete. The four reactions were combined. The mixture was filtered to get filter cake to give compound 1-9 (1.25 kg, crude, HCl) as a yellow solid. $^1$H NMR: 400 MHz DMSO-$d_6$ δ 9.04 (s, 1H), 4.02 (s, 2H), 3.88-3.94 (m, 1H), 3.09 (q, J=7.2 Hz, 2H), 2.09-2.14 (m, 2H), 1.61-1.84 (m, 8H), 1.19 (t, J=7.2 Hz, 3H).

Preparation 2: (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methanol M

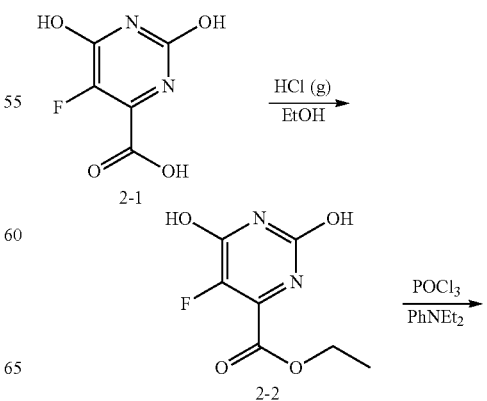

-continued

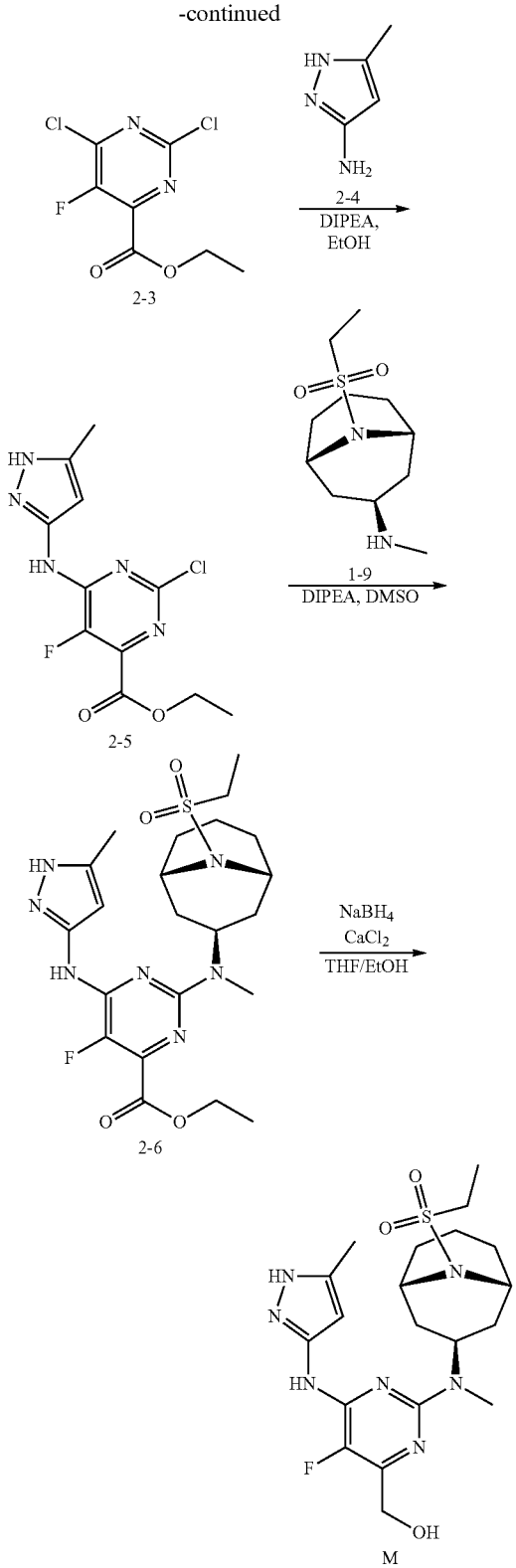

Step 1: A solution of compound 2-1 (1.00 kg, 5.74 mol, 1.0 eq) in ethanol (15.0 L) with saturated HCl (1.40 kg, 38.4 mol) was stirred at 90° C. for 60 h. HPLC showed one main peak was detected. The reaction mixture was filtered. The filter cake was collected to give compound 2-2 (1.00 kg, 81.8% yield, 98.8% purity) as a white solid. $^1$H NMR: 400 MHz DMSO-d$_6$ δ 11.82 (br s, 1H), 10.82 (br s, 1H), 4.31 (q, J=7.2 Hz, 2H), 1.27 (t, J=6.8 Hz, 3H).

Step 2: Five reactions were carried out in parallel. To a solution of compound 2-2 (560 g, 2.77 mol, 1.0 eq) in POCl$_3$ (1.68 L) was added N, N-diethylaniline (289 g, 1.94 mol, 0.7 eq). The mixture was stirred at 140° C. for 12 h. TLC (petroleum ether:ethyl acetate=10:1, product R$_f$=0.50) indicated compound 2-2 was consumed completely. The five reactions were combined. The reaction mixture was concentrated under reduced pressure to give a residue. The residue was diluted with ethyl acetate (25.0 L). The solution was poured into crushed ice (25.0 L). The water phase was extracted with ethyl acetate (25.0 L). The combined organic layers were washed with saturated sodium carbonate solution (10.0 L×2), dried over sodium sulfate, filtered and concentrated under reduced pressure to give a residue. The residue was purified by column chromatography (SiO$_2$, petroleum ether:ethyl acetate=1:0-50:1) to give compound 2-3 (2.00 kg) as a brown liquid. $^1$H NMR: 400 MHz CDCl$_3$ δ 4.51 (q, J=7.2 Hz, 2H), 1.44 (t, J=7.2 Hz, 3H).

Step 3: Four reactions were carried out in parallel. A mixture of compound 2-3 (480 g, 2.01 mol, 1.0 eq), compound 2-4 (224 g, 2.31 mol, 1.15 eq), DIPEA (519 g, 4.02 mol, 2.0 eq) in ethanol (2.60 L) was degassed and purged with N$_2$ for 3 times, and then the mixture was stirred at 25° C. for 4 h under N$_2$ atmosphere. TLC (petroleum ether:ethyl acetate=10:1) indicated compound 2-3 was consumed completely. TLC (petroleum ether:ethyl acetate=1:1, product R$_f$=0.40) indicated one new spot formed. The four reactions were combined. The reaction mixture was filtered and the filter cake was collected. The filtrate was concentrated under reduced pressure to give a residue. The residue was triturated with water (38.0 L) and filtered. The filter cake (300 g) was triturated with ethanol (600 mL) and filtered. The two filter cakes were combined to give compound 2-5 (1.50 kg, 62.2% yield) as a yellow solid. $^1$H NMR: 400 MHz DMSO-d$_6$ δ 12.31 (s, 1H), 10.76 (s, 1H), 6.38 (s, 1H), 4.35 (q, J=7.2 Hz, 2H), 2.27 (s, 3H), 1.30 (t, J=7.2 Hz, 3H).

Step 4: Four reactions were carried out in parallel. A solution of compound 2-5 (254 g, 848 mmol, 1.0 eq), compound 1-9 (300 g, 1.06 mol, HCl, 1.25 eq) and DIPEA (548 g, 4.24 mol, 5.0 eq) in DMSO (600 mL) was stirred at 130° C. for 16 h. TLC (ethyl acetate:petroleum ether=2:1, R$_f$=0.30) and LCMS showed ~9% of the starting material remained. The mixture was cooled to 25° C. The four reactions were combined, poured into ice water (12.0 L). A yellow precipitate was formed. The solid was collected by filtration to give compound 2-6 (1.50 kg, ~76% purity) as a yellow solid. (m/z): [M+H]$^+$ calcd for C$_{22}$H$_{32}$FN$_7$O$_4$S 510.22 found 510.2.

A suspension of compound 2-6 (440 g, 656 mmol, ~76% purity) in ethanol (1.10 L) was heated to 95° C. until the solid was dissolved. The solution was cooled to 25° C. and stirred for 12 h. HPLC showed ~96.9% purity. The three reactions were combined. The suspension was filtered to get the filter cake to give compound 2-6 (~570 g, 96.9% purity) as a light yellow solid. The product was used for the next step directly. $^1$H NMR: 400 MHz DMSO-d$_6$ δ 12.12 (s, 1H), 9.73 (s, 1H), 6.35 (s, 1H), 5.59 (br s, 1H), 4.32 (m, 2H), 4.02 (s, 2H), 3.13 (q, J=7.2 Hz, 2H), 2.83 (s, 3H), 2.20 (s, 3H), 1.94 (s, 3H), 1.64-1.73 (m, 5H), 1.76-1.87 (m, 5H), 1.29 (t, J=7.2 Hz, 3H), 1.21 (t, J=7.2 Hz, 3H).

Step 5: Five reactions were carried out in parallel. To a solution of compound 2-6 (130 g, 255 mmol, 1.0 eq) in tetrohydrofuran (3.25 L) and ethanol (3.25 L) was added NaBH$_4$ (77.2 g, 2.04 mol, 8.0 eq) and CaCl$_2$ (113 g, 1.02 mol, 4.0 eq) portion-wise at 0° C. The mixture was warmed to 10° C. and stirred for 2 h. TLC (ethyl acetate:petroleum ether=3:1, product R$_f$=0.20) showed the reaction was complete. The five reactions were combined. The mixture was quenched by saturated sodium carbonate solution (6.00 L), diluted with ethyl acetate (15.0 L) and stirred for 0.5 h. The suspension was filtered to get filtrate. The organic layer was separated, and aqueous layer was extracted with ethyl acetate (5.00 L×2). The combined organic layer was washed with brine (5.00 L), dried over sodium sulfate, filtered and concentrated to give compound M (500 g, crude) as a light yellow solid.

Purification: Five reactions were carried out in parallel. A suspension of M (100 g, 210 mmol) in ethanol (3.00 L) was heated to 95° C. until the solid was dissolved. The solution was cooled to 25° C. and stirred for 12 h, a lot of precipitate formed. HPLC showed 100% purity. The five reactions were combined. The solid was collected by filtration to give a total of 330 g of compound M (99.3% purity) as a light yellow solid (crystalline Form I). (m/z): [M+H]$^+$ calcd for C$_{20}$H$_{30}$FN$_7$O$_3$S 468.21 found 468.3. $^1$H NMR: 400 MHz DMSO-d$_6$ δ 12.02 (s, 1H), 9.29 (s, 1H), 6.34 (s, 1H), 5.61 (br s, 1H), 5.02 (t, J=6.8 Hz, 1H), 4.33 (d, J=4.0 Hz, 2H), 4.02 (s, 2H), 3.12 (q, J=7.2 Hz, 2H), 2.84 (s, 3H), 2.19 (s, 3H), 1.82-2.01 (m, 3H), 1.63-1.74 (m, 5H), 1.21 (t, J=7.2 Hz, 3H).

Preparation 3: ethyl 5-fluoro-2,6-dihydroxypyrimidine-4-carboxylate

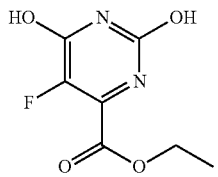

A solution of 5-fluoro-2,6-dihydroxypyrimidine-4-carboxylic acid (20.4 g, 120 mmol) in DMF (200 mL) was treated with DBU (18.7 g, 123 mmol) and was stirred for 0.5 h at 25° C. Then EtI (19.2 g, 123 mmol) was added and the resulting solution was heated to 60° C. for 3 hours. H$_2$O (1000 mL) was added to the mixture, and the resulting precipitate was collected by filtration, washed with H$_2$O (200 mL), and dried to give ethyl 5-fluoro-2,6-dihydroxypyrimidine-4-carboxylate (19 g, 80% yield).

Preparation 4: ethyl 2,6-dichloro-5-fluoropyrimidine-4-carboxylate

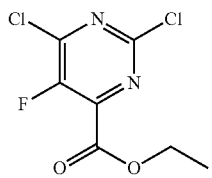

A mixture of ethyl 5-fluoro-2,6-dihydroxypyrimidine-4-carboxylate (5 g, 24.8 mmol), PhNEt$_2$ (2.58 g, 17.3 mmol), POCl$_3$ (130 g, 855.9 mmol) was heated to 100° C. for 4 hours. Then the reaction mixture was cooled to room temperature and poured into ice water (500 mL). The aqueous layer was extracted with EtOAc (1000 mL) and the organic layer was washed with sat. NaHCO$_3$ (200 mL), brine (200 mL), dried over Na$_2$SO$_4$, filtered, and concentrated under vacuum. The residue was purified by column chromatography (80 g column; 0-50% EtOAc in hexanes) to give ethyl 2,6-dichloro-5-fluoropyrimidine-4-carboxylate as yellow oil (3.8 g, 65%).

Preparation 5: ethyl 2-chloro-5-fluoro-6-((5-methyl-1H-pyrazol-3-yl)amino)pyrimidine-4-carboxylate

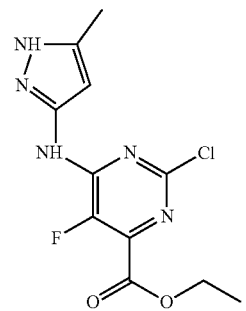 [SMILES: CCOC(=O)c1nc(Cl)nc(Nc2cc(C)[nH]n2)c1F]

A mixture of ethyl 2,6-dichloro-5-fluoropyrimidine-4-carboxylate (3.8 g, 16 mmol), 5-methyl-1H-pyrazol-3-amine (1.86 g, 19 mmol), and DIPEA (4 g, 32 mmol) in EtOH (100 mL) was stirred at r.t. for 2 h. The reaction mixture was concentrated under vacuum. Then water (500 mL) was added and the reaction mixture was filtered and the filter cake was washed with 100 mL of H2O, and dried in vacuo to give ethyl 2-chloro-5-fluoro-6-((5-methyl-1H-pyrazol-3-yl)amino)pyrimidine-4-carboxylate (3.8 g 80% yield).

Preparation 6: tert-butyl (1R,3s,5S)-3-((4-(ethoxycarbonyl)-5-fluoro-6-((5-methyl-1H-pyrazol-3-yl)amino)pyrimidin-2-yl)(methyl)amino)-9-azabicyclo[3.3.1]nonane-9-carboxylate

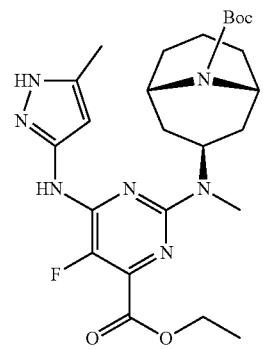 [SMILES: CCOC(=O)c1nc(N(C)[C@@H]2C[C@H]3CCC[C@@H](C2)N3C(=O)OC(C)(C)C)nc(Nc2cc(C)[nH]n2)c1F]

A mixture of ethyl 2-chloro-5-fluoro-6-((5-methyl-1H-pyrazol-3-yl)amino)pyrimidine-4-carboxylate (1.7 g, 5.684 mmol), tert-butyl (1R,3s,5S)-3-(methylamino)-9-azabicyclo[3.3.1]nonane-9-carboxylate (2.17 g, 8.527 mmol), and DIPEA (1.47 g, 11.368 mmol) in DMSO (50 mL) was heated to 110° C. for 18 h. The reaction mixture was poured into water (200 mL) and the reaction mixture was filtered and the filter cake was washed with 200 mL of H$_2$O and dried in vacuum to give crude tert-butyl (1R,3s,5S)-3-((4-(ethoxycarbonyl)-5-fluoro-6-((5-methyl-1H-pyrazol-3-yl)amino)pyrimidin-2-yl)(methyl)amino)-9-azabicyclo[3.3.1]nonane-9-carboxylate (3.5 g, crude). (m/z): [M+H]$^+$ calcd for $C_{25}H_{37}FN_7O_4$ 518.29 found 518.2.

Preparation 7: tert-butyl (1R,3s,5S)-3-((5-fluoro-4-(hydroxymethyl)-6-((5-methyl-1H-pyrazol-3-yl)amino)pyrimidin-2-yl)(methyl)amino)-9-azabicyclo[3.3.1]nonane-9-carboxylate

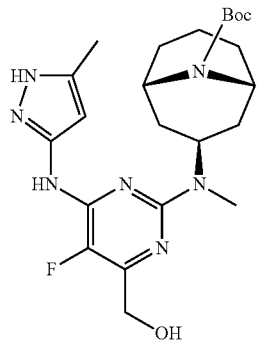 [SMILES: Cc1cc(Nc2nc(N(C)[C@@H]3C[C@H]4CCC[C@@H](C3)N4C(=O)OC(C)(C)C)nc(CO)c2F)n[nH]1]

A mixture of tert-butyl (1R,3s,5S)-3-((4-(ethoxycarbonyl)-5-fluoro-6-((5-methyl-1H-pyrazol-3-yl)amino)pyrimidin-2-yl)(methyl)amino)-9-azabicyclo[3.3.1]nonane-9-carboxylate (3.5 g, 7 mmol), NaBH$_4$ (2.1 g, 56 mmol), and CaCl$_2$ (3.1 g, 28 mmol) in a mixture of EtOH (50 mL) and THF (50 mL) was stirred overnight at 25° C. The reaction mixture was quench with Na$_2$CO$_3$ (aq) (80 mL) and H$_2$O (80 mL), the aqueous layer was extracted with EtOAc (100 mL×3) and the combined organic layers were washed with brine, dried over Na$_2$SO$_4$, and concentrated under vacuum. The residue was purified by prep-HPLC to give tert-butyl (1R,3s,5S)-3-((5-fluoro-4-(hydroxymethyl)-6-((5-methyl-1H-pyrazol-3-yl)amino)pyrimidin-2-yl)(methyl)amino)-9-azabicyclo[3.3.1]nonane-9-carboxylate (1.4 g, 44%). (m/z): [M+H]$^+$ calcd for $C_{23}H_{35}FN_7O_3$ 476.28 found 476.3.

Preparation 8: (2-(((1R,3s,5S)-9-azabicyclo[3.3.1]nonan-3-yl)(methyl)amino)-5-fluoro-6-((5-methyl-1H-pyrazol-3-yl)amino)pyrimidin-4-yl)methanol

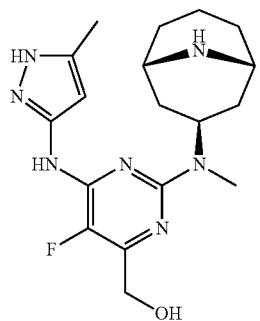 [SMILES: Cc1cc(Nc2nc(N(C)[C@@H]3C[C@H]4CCC[C@@H](C3)N4)nc(CO)c2F)n[nH]1]

A solution of tert-butyl(1R,3s,5S)-3-((5-fluoro-4-(hydroxymethyl)-6-((5-methyl-1H-pyrazol-3-yl)amino)pyrimidin-2-yl)(methyl)amino)-9-azabicyclo[3.3.1]nonane-9-carboxylate (1.4 g, 2.95 mmol) in HCl/dioxane (50 mL) was stirred at 25° C. for 4 h. The reaction mixture was filtered and the filter cake was washed with 100 mL of EtOAc and dried in vacuum to give (2-(((1R,3s,5S)-9-azabicyclo[3.3.1]nonan-3-yl)(methyl)amino)-5-fluoro-6-((5-methyl-1H-pyrazol-3-yl)amino)pyrimidin-4-yl)methanol (1.4 g, 100%). (m/z): [M+H]$^+$ calcd for $C_{18}H_{27}FN_7O$ 376.23 found 376.2.

Preparation 9: (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methanol

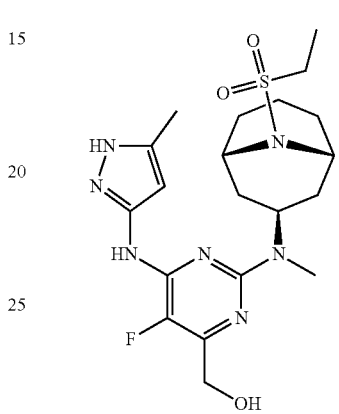

M (2-(((1R,3s,5S)-9-azabicyclo[3.3.1]nonan-3-yl(methyl)amino)-5-fluoro-6-((5-methyl-1H-pyrazol-3-yl)amino)pyrimidin-4-yl)methanol (95 mg, 0.253 mmol) was dissolved in Pyridine (4.0 ml) and treated with ethanesulfonyl chloride (0.024 ml, 0.253 mmol). The reaction mixture was stirred for 2 hours and subsequently concentrated in vacuo. The crude residue was dissolved in 3 mL of a 1:1 mixture of acetic acid/water, filtered to remove particulate, and purified by preparative HPLC (Agilent Dynamax 250×21.4 mm 10 µm, 15 mL/min, 2-50% ACN+0.05% TFA/ACN) using a 2-50% gradient of ACN in water with 0.05% TFA). Pure fractions were combined and lyophilized to provide the TFA salt of the title compound (12.92 mg, 8.8% yield, 99.9% purity). (m/z): [M+H]$^+$ calcd for $C_{20}H_{31}FN_7O_3S$ 468.22 found 468.

General Procedure 1: Acylation of Primary Alcohol

An acyl chloride (3.0 equiv., 0.77 mmol) was added to a mixture of (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methanol (1.0 equiv., 0.12 g, 0.26 mmol), diisopropylethylamine (3 equiv., 0.134 mL, 0.77 mmol), and N,N-dimethylaminopyridine (0.1 equiv., 3.1 mg, 0.026 mmol) in DMF (3.0 mL). The mixture was stirred at ambient temperature for 1.5 h. Hydrazine (4.5 equiv., 0.036 mL, 1.2 mmol) was added, and the mixture was stirred at ambient temperature for 30 min. Acetic acid (10 equiv., 0.147 mL, 2.6 mmol) was added, and the mixture was concentrated.

General Procedure 2: Formation of Free-Base Amorphous Solids

The trifluoroacetic acid salt of the desired compound was dissolved in MeOH (2.5 mL), and immobilized bicarbonate resin (PL-HCO$_3$ MP Resin (100 Å, 2.08 mmol/g, 150-300 µm)) was added. The mixture was agitated on a mechanical shaker at ambient temperature for 2 h. The resin was removed by filtration, and the filtrate was concentrated to give free-base amorphous solid.

Example 1: Preparation of (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methyl acetate

Example 2: Preparation of (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methyl propionate

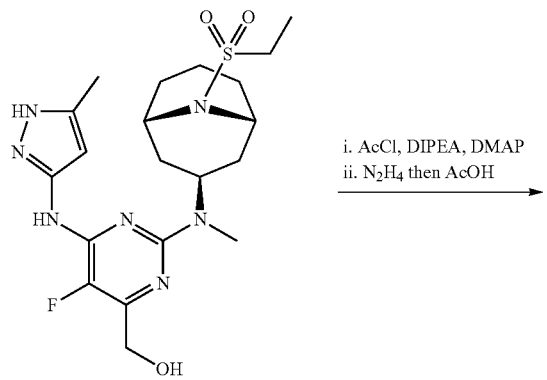

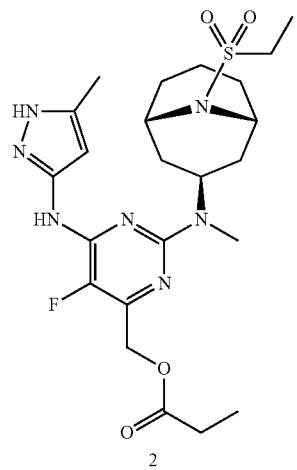

Compound 1 was prepared following general procedure 1, using acetyl chloride (0.055 mL, 0.77 mmol). The remaining residue was purified by normal-phase column chromatography (silica gel flash column, 0-10% MeOH/DCM), followed by reverse-phase column chromatography (RediSep Prep C18 column, 20-60% H$_2$O/CH$_3$CN). The free-base form of the desired compound was generated following general procedure 2, using immobilized bicarbonate resin (0.38 g, 0.78 mmol) to afford the desired product as an amorphous white solid (0.062 g, 0.12 mmol, 47% yield). LC-MS: m/z [M+H]$^+$=510.2 (calculated: 510.22); $^1$H NMR: 400 MHz DMSO-d$_6$ δ 12.04 (s, 1H), 9.44 (s, 1H), 6.32 (s, 1H), 5.58 (s, 1H), 4.97 (s, 2H), 4.02 (app. s, 2H), 3.12 (q, J=7.3 Hz, 2H), 2.81 (s, 3H), 2.19 (s, 3H), 2.08 (s, 3H), 1.96 (m, 3H), 1.86 (m, 2H), 1.67 (m, 5H), 1.21 (t, J=7.3 Hz, 3H).

Compound 2 was prepared following general procedure 1, using propionyl chloride (0.067 mL, 0.77 mmol). The remaining residue was purified by reverse-phase column chromatography (RediSep Prep C18 column, 25-60% H$_2$O/CH$_3$CN). The free-base form of the desired compound was generated following general procedure 2, using immobilized bicarbonate resin (0.45 g, 0.94 mmol) to afford the desired product as an amorphous white solid (0.087 g, 0.16 mmol, 62% yield). LC-MS: m/z [M+H]$^+$=524.1 (calculated: 524.24); $^1$H NMR: 400 MHz DMSO-d$_6$ δ 12.04 (s, 1H), 9.42 (s, 1H), 6.33 (s, 1H), 5.58 (s, 1H), 4.99 (s, 2H), 4.02 (app. s, 2H), 3.12 (q, J=7.3 Hz, 2H), 2.80 (s, 3H), 2.38 (q, J=7.5 Hz, 2H), 2.19 (s, 3H), 1.96 (m, 3H), 1.85 (m, 2H), 1.67 (m, 5H), 1.21 (t, J=7.3 Hz, 3H), 1.06 (t, J=7.5 Hz, 3H).

Example 3: (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methyl butyrate

Example 4: (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methyl pentanoate

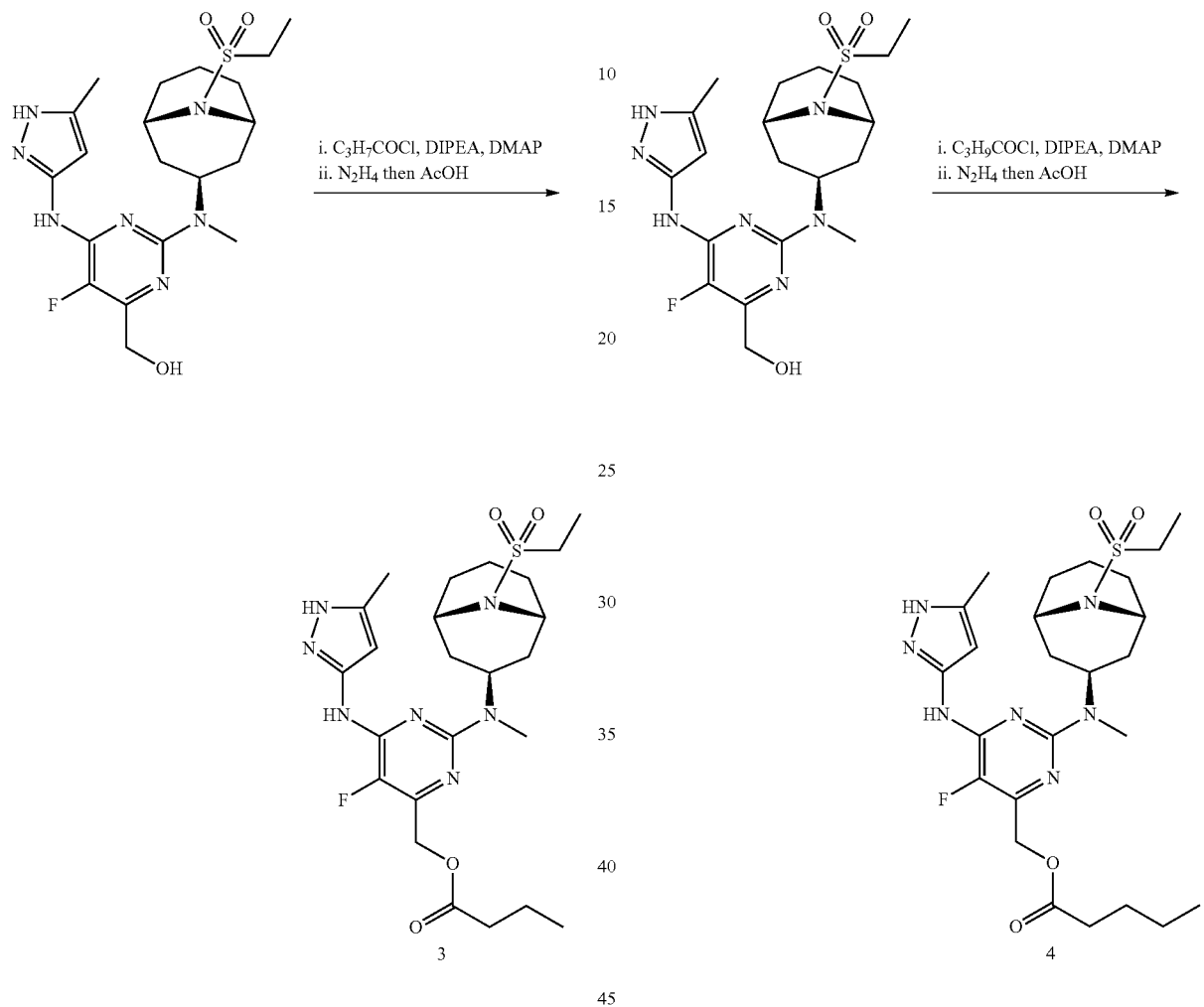

Compound 3 was prepared following general procedure 1, using butyryl chloride (0.081 mL, 0.77 mmol). The remaining residue was purified by normal-phase column chromatography (silica gel flash column, 0-10% MeOH/DCM), followed by reverse-phase column chromatography (RediSep Prep C18 column, 30-70% $H_2O/CH_3CN$). The free-base form of the desired compound was generated following general procedure 2, using immobilized bicarbonate resin (0.317 g, 0.66 mmol) to afford the desired product as an amorphous white solid (0.058 g, 0.11 mmol, 42% yield). LC-MS: m/z [M+H]$^+$=538.2 (calculated: 538.25); $^1$H NMR: 400 MHz DMSO-$d_6$ δ 12.05 (s, 1H), 9.46 (s, 1H), 6.33 (s, 1H), 5.58 (s, 1H), 4.99 (s, 2H), 4.01 (app. s, 2H), 3.12 (q, J=7.2 Hz, 2H), 2.80 (s, 3H), 2.34 (t, J=7.3 Hz, 2H), 2.19 (s, 3H), 1.96 (m, 3H), 1.85 (m, 2H), 1.66 (m, 5H), 1.56 (dt, J=14.6 Hz, 7.3 Hz, 2H), 1.21 (t, J=7.2 Hz, 3H), 0.89 (t, J=7.4 Hz, 3H).

Compound 4 was prepared following general procedure 1, using valeroyl chloride (0.093 mL, 0.77 mmol). The remaining residue was purified by normal-phase column chromatography (silica gel flash column, 0-10% MeOH/DCM), followed by reverse-phase column chromatography (RediSep Prep C18 column, 40-75% $H_2O/CH_3CN$). The free-base form of the desired compound was generated following general procedure 2, using immobilized bicarbonate resin (0.225 g, 0.47 mmol) to afford the desired product as an amorphous white solid (0.045 g, 0.082 mmol, 32% yield). LC-MS: m/z [M+H]$^+$=552.3 (calculated: 552.27); $^1$H NMR: 400 MHz DMSO-$d_6$ δ 12.04 (s, 1H), 9.42 (s, 1H), 6.33 (s, 1H), 5.59 (s, 1H), 4.98 (s, 2H), 4.02 (app. s, 2H), 3.12 (q, J=7.1 Hz, 2H), 2.80 (s, 3H), 2.36 (t, J=7.4 Hz, 2H), 2.19 (s, 3H), 1.96 (m, 3H), 1.86 (m, 2H), 1.66 (m, 5H), 1.53 (m, 2H), 1.31 (dt, J=14.9 Hz, 7.3 Hz, 2H), 1.20 (t, J=7.2 Hz, 3H), 0.86 (t, J=7.3 Hz, 3H).

Example 5: (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methyl heptanoate Example 6: cyclohexyl ((2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methyl) carbonate

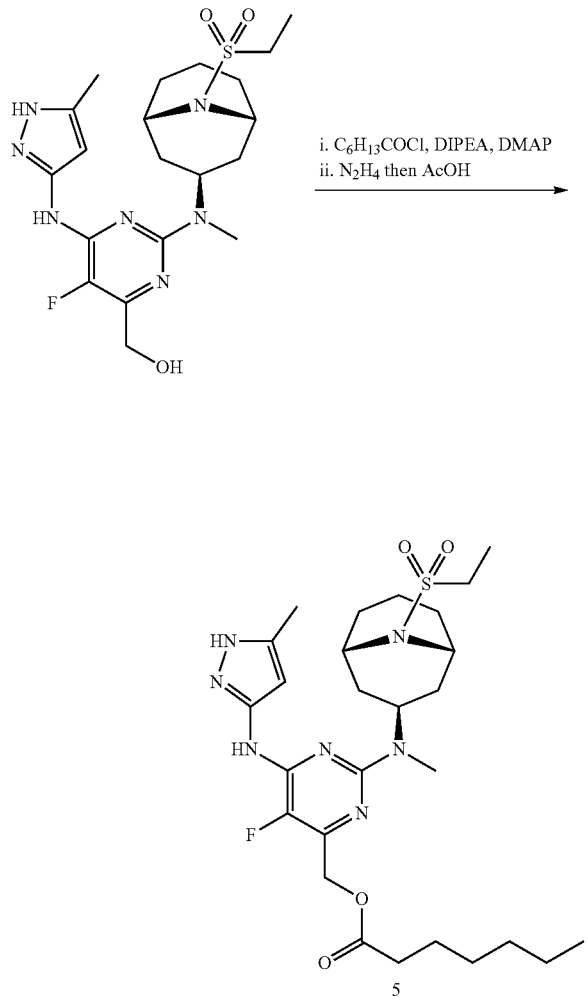

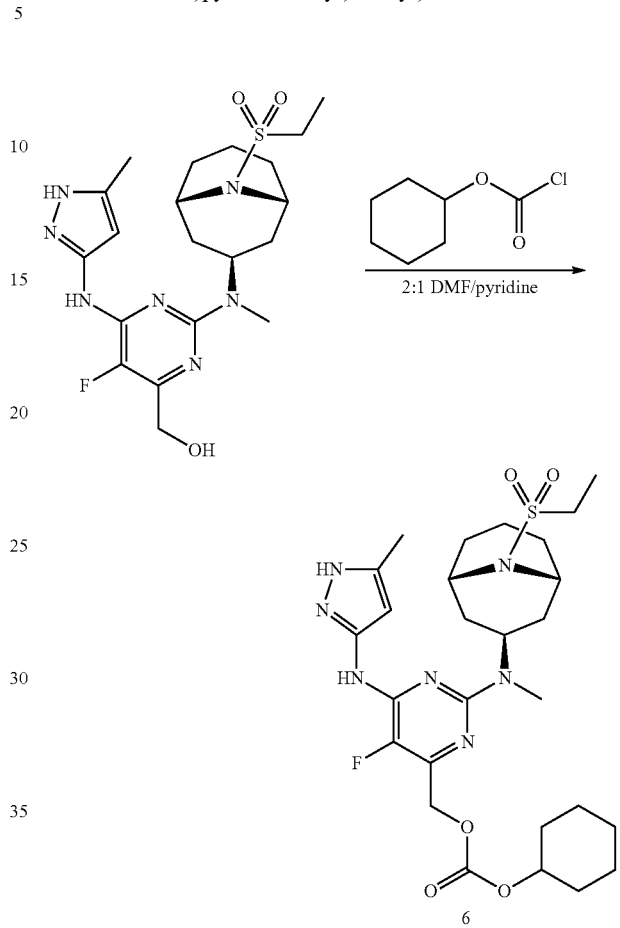

Compound 5 was prepared following general procedure 1, using heptanoyl chloride (0.12 mL, 0.77 mmol). The remaining residue was purified by normal-phase column chromatography (silica gel flash column, 0-10% MeOH/DCM), followed by reverse-phase column chromatography (RediSep Prep C18 column, 40-75% H$_2$O/CH$_3$CN). The free-base form of the desired compound was generated following general procedure 2, using immobilized bicarbonate resin (0.337 g, 0.701 mmol) to afford the desired product as an amorphous white solid (0.068 g, 0.12 mmol, 45% yield). LC-MS: m/z [M+H]$^+$=580.3 (calculated: 580.30); $^1$H NMR: 400 MHz DMSO-d$_6$ δ 12.04 (s, 1H), 9.44 (s, 1H), 6.31 (s, 1H), 5.59 (s, 1H), 4.98 (s, 2H), 4.02 (app. s, 2H), 3.11 (q, J=7.2 Hz, 2H), 2.80 (s, 3H), 2.35 (t, J=7.2 Hz, 2H), 2.19 (s, 3H), 1.96 (m, 3H), 1.85 (m, 2H), 1.69 (m, 5H), 1.53 (m, 2H), 1.22 (m, 9H), 0.84 (app. m, 3H).

A solution of (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methanol (1.0 equiv., 0.12 g, 0.26 mmol) in 2:1 DMF/pyridine (3.0 mL) was cooled on ice, and cyclohexyl chloroformate (3.0 equiv., 0.12 mL, 0.81 mmol) was added dropwise in 3 portions of 40 µL over 15 min. The mixture was stirred on ice for 4 h. Further cyclohexyl chloroformate (3.0 equiv., 0.12 mL, 0.81 mmol) was added dropwise in 2 portions of 60 µL over 10 min. The mixture was stirred on ice for 1 h. Hydrazine (15 equiv., 0.121 mL, 3.85 mmol) was added, and the mixture was stirred at ambient temperature for 35 min and concentrated. The remaining residue was purified by reverse-phase column chromatography (RediSep Prep C18 column, 40-75% H$_2$O/CH$_3$CN). The free-base form of the desired compound was generated following general procedure 2, using immobilized bicarbonate resin (0.46 g, 0.96 mmol) to afford the desired product as an amorphous white solid (0.085 g, 0.124 mmol, 54% yield). LC-MS: m/z [M+H]$^+$=594.3 (calculated: 594.28); $^1$H NMR: 400 MHz DMSO-d$_6$ δ 12.04 (s, 1H), 9.46 (s, 1H), 6.32 (s, 1H), 5.58 (s, 1H), 5.03 (s, 2H), 4.55 (tt, J=12.6 Hz, 4.2 Hz, 1H), 4.02 (app. s, 2H), 3.12 (q, J=7.3 Hz, 2H), 2.80 (s, 3H), 2.19 (s, 3H), 1.96 (m, 3H), 1.85 (m, 4H), 1.66 (m, 7H), 1.36 (m, 6H), 1.21 (t, J=7.3 Hz, 3H).

Example 7: (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methyl tetrahydro-2H-pyran-4-carboxylate

Example 8: (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methyl isopropyl carbonate

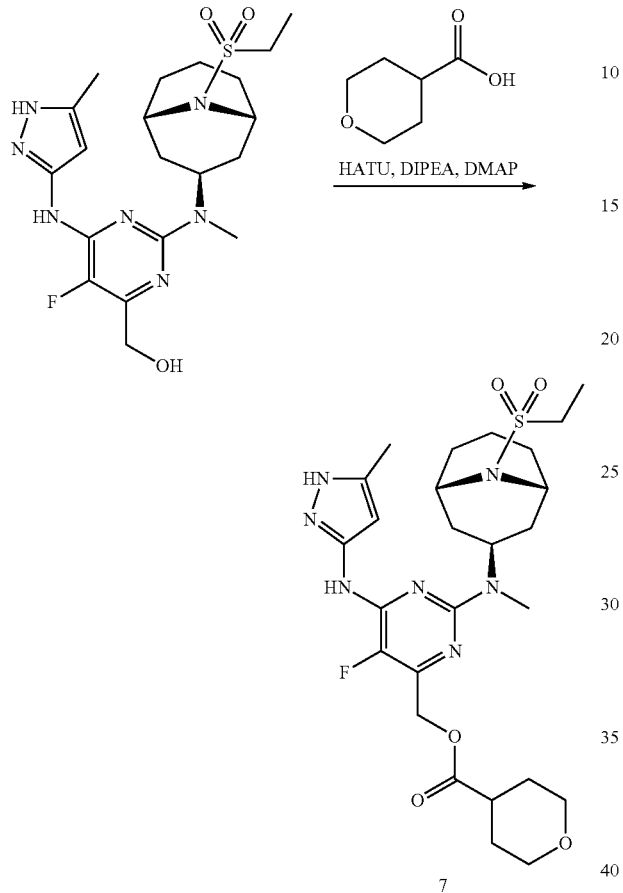

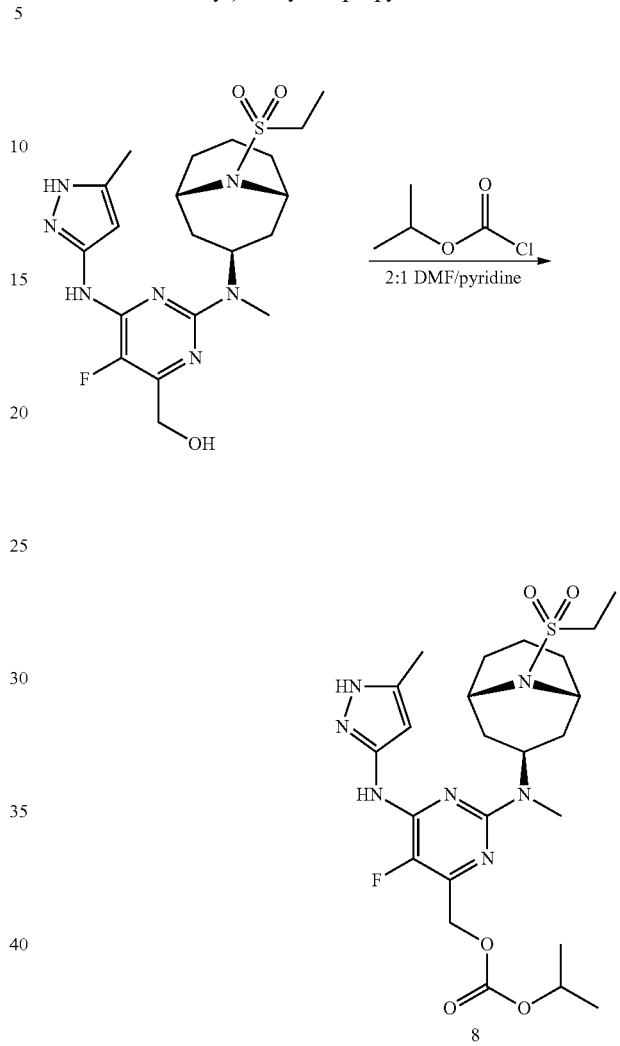

Diisopropylethylamine (4.0 equiv., 0.209 mL, 1.20 mmol) was added to a solution of (2-(((1R,3s,5 S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methanol (1.0 equiv., 0.14 g, 0.30 mmol), tetrahydropyran-4-carboxylic acid (2.5 equiv., 0.097 g, 0.75 mmol), and N,N-dimethylaminopyridine (0.2 equiv., 7.3 mg, 0.060 mmol) in DMF (3.0 mL), and the mixture was stirred at ambient temperature for 15 min. HATU (2.2 equiv., 0.25 g, 0.66 mmol) was added, and the mixture was stirred at ambient temperature for 16 h. Hydrazine (3 equiv., 0.028 mL, 0.90 mmol) was added, and the mixture was stirred at ambient temperature for 30 min. Acetic acid (10 equiv., 0.17 mL, 3.0 mmol) was added, and the mixture was concentrated. The remaining residue was purified by normal-phase column chromatography (silica gel flash column, 0-10% MeOH/DCM) to afford the desired product as an amorphous white solid (0.158 g, 0.27 mmol, 89% yield). LC-MS: m/z [M+H]$^+$=580.3 (calculated: 580.26); $^1$H NMR: 400 MHz DMSO-d$_6$ δ 12.04 (s, 1H), 9.43 (s, 1H), 6.32 (s, 1H), 5.57 (s, 1H), 5.02 (d, J=1.9 Hz, 2H), 4.02 (app. s, 2H), 3.82 (dt, J=11.4 Hz, 3.8 Hz, 2H), 3.36 (td, J=11.4 Hz, 2.4 Hz, 2H), 3.12 (q, J=7.2 Hz, 2H), 2.80 (s, 3H), 2.66 (m, 1H), 2.19 (s, 3H), 1.97 (m, 3H), 1.85 (m, 2H), 1.64 (m, 5H), 1.26 (app. q, J=5.9 Hz, 4H), 1.21 (t, J=7.3 Hz, 3H).

A solution of (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methanol (1.0 equiv., 0.14 g, 0.30 mmol) in 2:1 DMF/pyridine (3.0 mL) was cooled on ice, and isopropyl chloroformate (1.0 M solution in toluene, 2.5 equiv., 0.75 mL, 0.75 mmol) was added dropwise. The mixture was stirred on ice for 1 h. Further isopropyl chloroformate (1.0 M solution in toluene, 3.0 equiv., 0.90 mL, 0.90 mmol) was added dropwise, and the mixture was stirred at ambient temperature for 16 h. Hydrazine (10 equiv., 0.094 mL, 3.0 mmol) was added, and the mixture was stirred at ambient temperature for 2.5 h and concentrated. The remaining residue was purified by normal-phase column chromatography (silica gel flash column, 0-10% MeOH/DCM) to afford the desired product as an amorphous white solid (0.094 g, 0.17 mmol, 56% yield). LC-MS: m/z [M+H]$^+$=554.3 (calculated: 554.25); $^1$H NMR: 400 MHz DMSO-d$_6$ δ 12.05 (s, 1H), 9.46 (s, 1H), 6.33 (s, 1H), 5.57 (s, 1H), 5.02 (d, J=1.8 Hz, 2H), 4.77 (sep, 1H), 4.02 (app. s, 2H), 3.12 (q, J=7.3 Hz, 2H), 2.80 (s, 3H), 2.19 (s, 3H), 1.96 (m, 3H), 1.85 (m, 2H), 1.67 (m, 5H), 1.22 (d, J=6.4 Hz, 6H), 1.21 (t, J=7.2 Hz, 3H).

Example 9: (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methyl (tetrahydro-2H-pyran-4-yl) carbonate

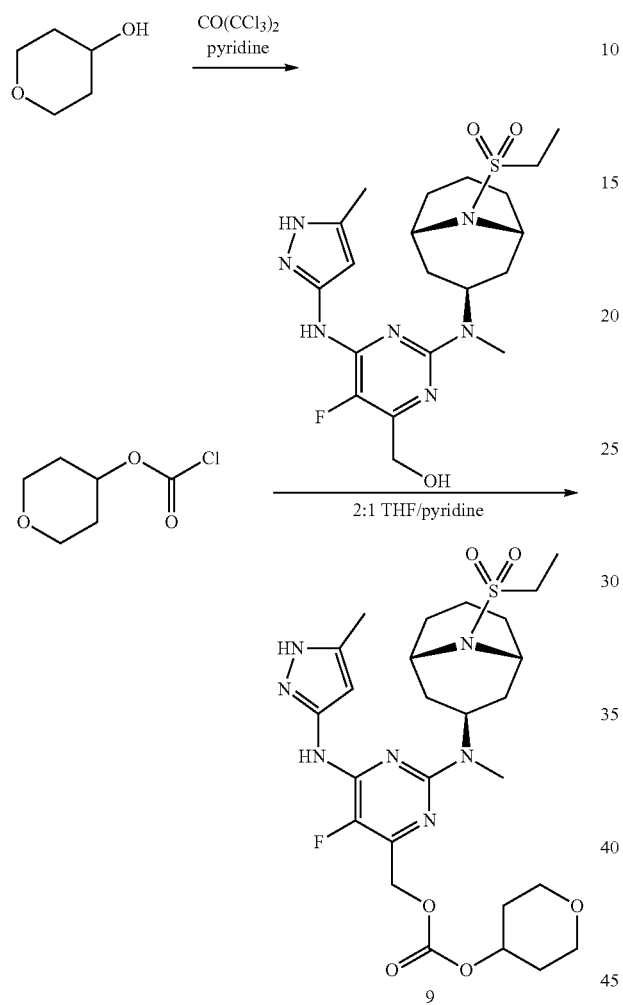

A solution of pyridine (0.63 mL, 7.8 mmol) in THF (4.0 mL) was added dropwise to an ice-cooled solution of triphosgene (0.77 g, 2.6 mmol) in THF (9.0 mL). The mixture was stirred on ice for 10 min. A solution of tetrahydro-4-pyranol (0.47 mL, 4.9 mmol) in THF (7.0 mL) was added, and the mixture was stirred at ambient temperature for 1 h. The mixture was diluted with EtOAc (25 mL) and washed with water (35 mL), followed by 0.2 M aq. HCl (25 mL) and brine (25 mL). The organic layer was dried over $Na_2SO_4$, filtered, and concentrated to afford a pale orange liquid, which was used without further purification in the subsequent step (0.80 g, 4.9 mmol, 99% yield).

A solution of (2-(((1R,3s,5S)-9-(ethylsulfonyl)-9-azabicyclo[3.3.1]nonan-3-yl)(methyl)amino)-5-fluoro-6-((5-methyl-1H-pyrazol-3-yl)amino)pyrimidin-4-yl)methanol (1.0 equiv., 0.14 g, 0.30 mmol) in 2:1 THF/pyridine (3.0 mL) was cooled on ice, and a solution of tetrahydro-2H-pyran-4-yl carbonochloridate (4.0 equiv., 0.20 g, 1.2 mmol) in THF (0.5 mL) was added dropwise. The mixture was stirred at ambient temperature for 1.5 h and subsequently at 60° C. for 1.5 h. Further tetrahydro-2H-pyran-4-yl carbonochloridate (4.0 equiv., 0.20 g, 1.2 mmol) in THF (0.5 mL) was added, and the mixture was stirred at 60° C. for 16 h. Hydrazine (24 equiv., 0.23 mL, 7.2 mmol) was added, and the mixture was stirred at ambient temperature for 35 min. The mixture was concentrated, and the remaining residue was purified by normal-phase column chromatography (silica gel flash column, 0-5% MeOH/DCM) to afford the desired product as an amorphous white solid (0.132 g, 0.22 mmol, 73% yield). LC-MS: m/z [M+H]$^+$=596.2 (calculated: 596.26); $^1$H NMR: 400 MHz DMSO-d$_6$ δ 12.05 (s, 1H), 9.46 (s, 1H), 6.33 (s, 1H), 5.58 (s, 1H), 5.05 (d, J=1.6 Hz, 2H), 4.77 (sep, J=6.4 Hz, 1H), 4.02 (app. s, 2H), 3.77 (dt, J=11.6 Hz, 4.5 Hz, 2H), 3.44 (ddd, J=11.9 Hz, 9.3 Hz, 2.9 Hz, 2H), 3.12 (q, J=7.3 Hz, 2H), 2.80 (s, 3H), 2.19 (s, 3H), 1.93 (m, 7H), 1.63 (m, 7H), 1.21 (t, J=7.3 Hz, 3H).

Preparation 10: methyl 2-chloro-6-((5-methyl-1H-pyrazol-3-yl)amino)pyrimidine-4-carboxylate

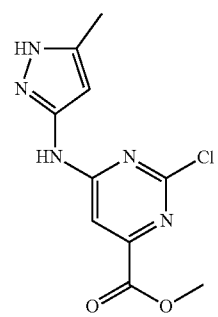 [SMILES: COC(=O)c1cc(Nc2cc(C)[nH]n2)nc(Cl)n1]

A mixture of 5-methyl-1H-pyrazol-3-amine (5.6 g, 58 mmol), methyl 2,6-dichloropyrimidine-4-carboxylate (12.0 g, 58 mmol), and DIPEA (15.0 g, 116 mmol) in DMSO (120 ml) was stirred at 25° C. for 12 hours. $H_2O$ (500 mL) was added and the precipitated solid was collected by filtration to give the title intermediate (15 g, 97%) as a yellow solid. (m/z): [M+H]$^+$ calcd for $C_{10}H_{11}ClN_5O_2$ 268.05 found 268.1.

Preparation 11: tert-butyl (1R,3s,5S)-3-((4-(methoxycarbonyl)-6-((5-methyl-1H-pyrazol-3-yl)amino)pyrimidin-2-yl)(methyl)amino)-9-azabicyclo[3.3.1]nonane-9-carboxylate

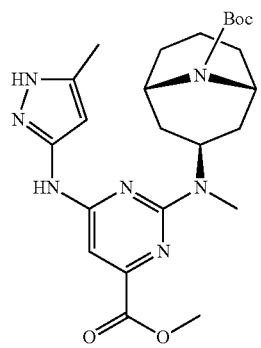 [SMILES: COC(=O)c1cc(Nc2cc(C)[nH]n2)nc(N(C)[C@@H]2C[C@H]3CCC[C@@H](C2)N3C(=O)OC(C)(C)C)n1]

A mixture of methyl 2-chloro-6-((5-methyl-1H-pyrazol-3-yl)amino)pyrimidine-4-carboxylate (12.0 g, 45 mmol), tert-butyl (1R,3s,5S)-3-(methylamino)-9-azabicyclo[3.3.1]

nonane-9-carboxylate (13.7 g, 54 mmol), and DIPEA (12.0 g, 90 mmol) in NMP (120 ml) was stirred at 120° C. for 16 hours. The reaction was poured into H₂O (2000 mL), the precipitated solid was collected by filtration to give the title intermediate (15 g, 68%) as a white solid. (m/z): [M+H]⁺ calcd for $C_{24}H_{36}N_7O_4$ 486.28 found 486.3.

Preparation 12: tert-butyl (1R,3s,5S)-3-((4-carbamoyl-6-((5-methyl-1H-pyrazol-3-yl)amino)pyrimidin-2-yl)(methyl)amino)-9-azabicyclo[3.3.1]nonane-9-carboxylate

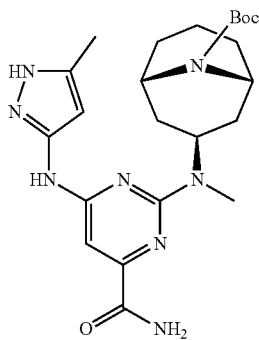 [SMILES: Cc1cc(Nc2cc(C(N)=O)nc(N(C)[C@@H]3C[C@H]4CCC[C@@H](C3)N4C(=O)OC(C)(C)C)n2)n[nH]1]

To tert-butyl (1R,3s,5S)-3-((4-(methoxycarbonyl)-6-((5-methyl-1H-pyrazol-3-yl)amino)pyrimidin-2-yl)(methyl)amino)-9-azabicyclo[3.3.1]nonane-9-carboxylate (3 batches of 2 g, 4.12 mmol) was added NH₃/MeOH (3 aliquots of 60 ml) in a 100 ml sealed tube, the reaction mixture was stirred at 25° C. for 12 hours. The reaction mixture was concentrated in vacuum to afford the title intermediate (3.7 g, 64%). (m/z): [M+H]⁺ calcd for $C_{23}H_{35}N_8O_3$ 471.28 found 471.3.

Preparation 13: 2-(((1R,3s,5S)-9-azabicyclo[3.3.1]nonan-3-yl)(methyl)amino)-6-((5-methyl-1H-pyrazol-3-yl)amino)pyrimidine-4-carboxamide

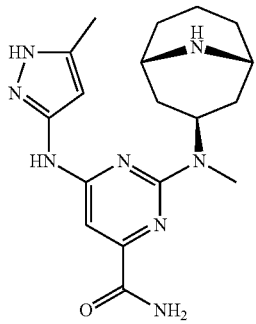 [SMILES: Cc1cc(Nc2cc(C(N)=O)nc(N(C)[C@@H]3C[C@H]4CCC[C@@H](C3)N4)n2)n[nH]1]

To a mixture of tert-butyl(1R,3s,5S)-3-((4-carbamoyl-6-((5-methyl-1H-pyrazol-3-yl)amino)pyrimidin-2-yl)(methyl)amino)-9-azabicyclo[3.3.1]nonane-9-carboxylate (3.7 g, 7.9 mmol) in dioxane (185 mL) was added HCl/Dioxane (37 mL). The reaction was stirred at 25° C. for 3 hours. TLC showed no starting material remained. The solvent was removed, and the crude product was washed with ethyl acetate/MeOH (100:1) to give the title intermediate as the HCl salt (4.0 g, 95%). (m/z): [M+H]⁺ calcd for $C_{18}H_{27}N_8O$ 371.23 found 371.1.

Preparation 14: 2-(((1R,3s,5S)-9-(ethylsulfonyl)-9-azabicyclo[3.3.1]nonan-3-yl)(methyl)amino)-6-((5-methyl-1H-pyrazol-3-yl)amino)pyrimidine-4-carboxamide (C-1)

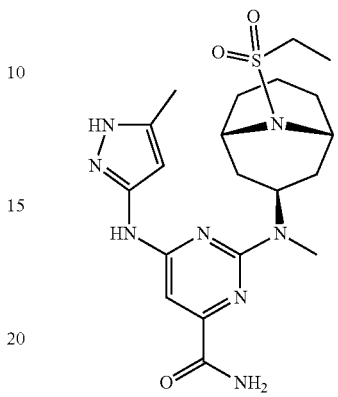

2-((1R,3s,5S)-9-azabicyclo[3.3.1]nonan-3-yl(methyl)amino)-6-((5-methyl-1H-pyrazol-3-yl)amino)pyrimidine-4-carboxamide (40 mg, 0.108 mmol) and DIPEA (0.057 ml, 0.324 mmol) were dissolved in DMF (1.50 ml) and cooled to 0° C. Ethane sulfonyl chloride was added and the reaction mixture was allowed to warm to room temperature and stirred for 72 hours. The reaction mixture was concentrated in vacuo and crude product was purified by preparative reverse phase HPLC (Agilent Dynamax 250×21.4 mm 10 μm, 15 mL/min, 2-70% ACN+0.1% TFA/ACN) to provide the TFA salt of the title compound (4.5 mg, 9.01%). (m/z): [M+H]⁺ calcd for $C_{20}H_{31}N_8O_3S$ 463.22 found 463.2.

Preparation 15: tert-butyl (1R,3s,5S)-3-((4-(methoxycarbonyl)-6-((5-methyl-1H-pyrazol-3-yl)amino)pyrimidin-2-yl)(methyl)amino)-8-azabicyclo[3.2.1]octane-8-carboxylate

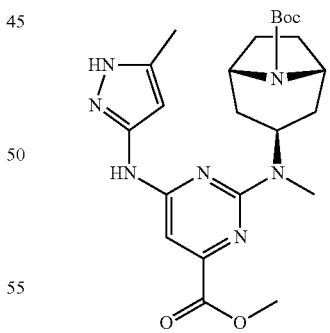

A mixture of methyl 2-chloro-6-((5-methyl-1H-pyrazol-3-yl)amino)pyrimidine-4-carboxylate (8.3 g, 31.0 mmol), tert-butyl (1R,3s,5S)-3-(methylamino)-8-azabicyclo[3.2.1]octane-8-carboxylate (8.2 g, 34.1 mmol), and DIPEA (10.8 mL, 62.0 mmol) in DMSO (85 ml) was stirred at 120° C. for 16 hours. The mixture was poured into 2 L of water, stirred vigorously, and then filtered to afford the title compound (11.1 g, 76%). (m/z): [M+H]⁺ calcd for $C_{23}H_{34}N_7O_4$ 472.27 found 472.3.

Preparation 16: tert-butyl (1R,3s,5S)-3-((4-(hydroxymethyl)-6-((5-methyl-1H-pyrazol-3-yl)amino)pyrimidin-2-yl)(methyl)amino)-8-azabicyclo[3.2.1]octane-8-carboxylate

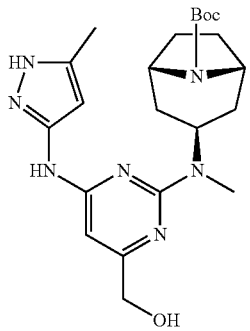 [SMILES: Cc1cc(Nc2cc(CO)nc(N(C)[C@@H]3C[C@H]4CC[C@@H](C3)N4C(=O)OC(C)(C)C)n2)n[nH]1]

To a mixture of NaBH$_4$ (8 g, 212 mmol) in MeOH (100 mL) was added tert-butyl (1R,3s,5S)-3-((4-(methoxycarbonyl)-6-((5-methyl-1H-pyrazol-3-yl)amino)pyrimidin-2-yl)(methyl)amino)-8-azabicyclo[3.2.1]octane-8-carboxylate (10 g, 21.2 mmol) in THF (100 mL) at 0° C. The reaction mixture was then heated to reflux for 1 h. The reaction was quenched with water (500 mL), and the mixture extracted with ethyl acetate (3×200 mL). The combined organic layers were washed with brine (1×100 mL), dried over anhydrous Na$_2$SO$_4$, and concentrated in vacuo. The crude residue was purified by flash chromatography on silica gel (Petroleum ether:ethyl acetate=4:1) to afford the title compound (7 g, 68%). (m/z): [M+H]$^+$ calcd for C$_{22}$H$_{34}$N$_7$O$_3$ 444.27 found 444.3.

Preparation 17: (2-(((1R,3s,5S)-8-azabicyclo[3.2.1]octan-3-yl)(methyl)amino)-6-((5-methyl-1H-pyrazol-3-yl)amino)pyrimidin-4-yl)methanol

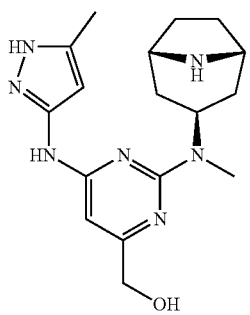 [SMILES: Cc1cc(Nc2cc(CO)nc(N(C)[C@@H]3C[C@H]4CC[C@@H](C3)N4)n2)n[nH]1]

A mixture of tert-butyl (1R,3s,5S)-3-((4-(hydroxymethyl)-6-((5-methyl-1H-pyrazol-3-yl)amino)pyrimidin-2-yl)(methyl)amino)-8-azabicyclo[3.2.1]octane-8-carboxylate (6.5 g, 14.7 mmol) in HCl/dioxane (100 mL) was stirred at r.t. for 1 h. The mixture was concentrated in vacuum to afford the HCl salt of the title intermediate (4.8 g, 100%). (m/z): [M+H]$^+$ calcd for C$_{17}$H$_{26}$N$_7$O 344.22 found 344.1.

Preparation 18: 3-(((1R,3s,5S)-3-((4-(hydroxymethyl)-6-((5-methyl-1H-pyrazol-3-yl)amino)pyrimidin-2-yl)(methyl)amino)-8-azabicyclo[3.2.1]octan-8-yl)propanenitrile (C-2)

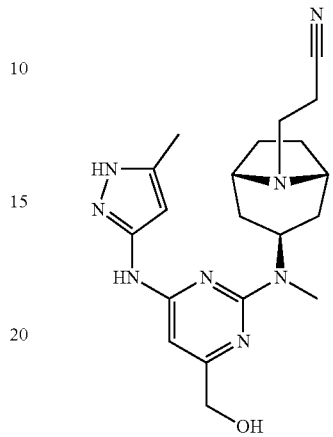

(2-(((1R,3s,5S)-8-azabicyclo[3.2.1]octan-3-yl)(methyl)amino)-6-((5-methyl-1H-pyrazol-3-yl)amino)pyrimidin-4-yl)methanol (50 mg, 0.146 mmol) and DIPEA (0.076 ml, 0.437 mmol) were dissolved in MeOH (1.50 ml). Acrylonitrile (0.014 ml, 0.218 mmol) was added and the reaction mixture was stirred at room temperature for 90 min. The reaction mixture was then concentrated in vacuo and the crude residue was purified by preparative reverse phase HPLC (Agilent Dynamax 250×21.4 mm 10 μm, 15 mL/min, 2-60% ACN+0.1% TFA/ACN) to provide the TFA salt of the title compound (14 mg, 19%). (m/z): [M+H]$^+$ calcd for C$_{20}$H$_{29}$N$_8$O 397.25 found 397.1.

Biological Assays

Assay 1: Biochemical JAK and Tyk2 Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM MgCl$_2$, and 1 mM EGTA). Recombinant GST-tagged JAK enzymes and a GFP-tagged STAT1 peptide substrate were obtained from Life Technologies.

Serially or discretely diluted compounds were pre-incubated with each of the four JAK enzymes and the substrate in white 384-well microplates (Corning) at ambient temperature for 1 h. ATP was subsequently added to initiate the kinase reactions in 10 μL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 μM, 3 μM, 1.6 μM, and 10 μM; while the substrate concentration is 200 nM for all four assays. Kinase reactions were allowed to proceed for 1 hour at ambient temperature before a 10 μL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and IC$_{50}$ values were determined from a 4-parameter robust fit model with the Prism software (GraphPad Software). Results were expressed as pIC$_{50}$ (negative logarithm of IC50) and subsequently converted to pKi (negative logarithm of dissociation constant, Ki) using the Cheng-Prusoff equation.

Assay 2: Inhibition of IL-2 Stimulated pSTAT5 in Tall-1 T Cells

The potency of test compounds for inhibition of interleukin-2 (IL-2) stimulated STATS phosphorylation was measured in the Tall-1 human T cell line (DSMZ) using AlphaLisa. Because IL-2 signals through JAK1/3, this assay provides a measure of JAK1/3 cellular potency.

Phosphorylated STAT5 was measured via the AlphaLISA SureFire Ultra pSTAT5 (Tyr694/699) kit (PerkinElmer). Human T cells from the Tall-1 cell line were cultured in a 37° C., 5% CO$_2$ humidified incubator in RPMI (Life Technologies) supplemented with 15% Heat Inactivated Fetal Bovine Serum (FBS, Life Technologies), 2 mM Glutamax (Life Technologies), 25 mM HEPES (Life Technologies) and 1× Pen/Strep (Life Technologies). Compounds were serially diluted in DMSO and dispensed acoustically to empty wells. Assay media (phenol red-free DMEM (Life Technologies) supplemented with 10% FBS (ATCC)) was dispensed (4 µL/well) and plates shaken at 900 rpm for 10 mins. Cells were seeded at 45,000 cells/well in assay media (4 µL/well), and incubated at 37° C., 5% CO$_2$ for 1 hour, followed by the addition of IL-2 (R&D Systems; final concentration 300 ng/mL) in pre-warmed assay media (4 µL) for 30 minutes. After cytokine stimulation, cells were lysed with 6 ul of 3× AlphaLisa Lysis Buffer (PerkinElmer) containing 1× PhosStop and Complete tablets (Roche). The lysate was shaken at 900 rpm for 10 minutes at room temperature (RT). Phosphorylated STAT5 was measured via the pSTAT5 AlphaLisa kit (PerkinElmer). Freshly prepared acceptor bead mixture was dispensed onto lysate (5 µL) under green filtered <100 lux light. Plates were shaken at 900 rpm for 2 mins, briefly spun down, and incubated for 2 hrs at RT in the dark. Donor beads were dispensed (5 µL) under green filtered <100 lux light. Plates were shaken at 900 rpm for 2 minutes, briefly spun down, and incubated overnight at RT in the dark. Luminescence was measured with excitation at 689 nm and emission at 570 nm using an EnVision plate r reader (PerkinElmer) under green filtered <100 lux light.

To determine the inhibitory potency of test compounds in response to IL-2, the average emission intensity of beads bound to pSTAT5 was measured in a human T cell line. IC$_{50}$ values were determined from analysis of the inhibition curves of signal intensity versus compound concentration. Data are expressed as pIC$_{50}$ (negative decadic logarithm IC$_{50}$) values (mean±standard deviation).

In Vitro Assay Results

The compounds of the disclosure were tested in one or more of the assays described above.

In Table 1 below, for the JAK1, JAK 2, JAK3, and TYK2 enzyme assays, A represents a pK$_i$ value ≥10 (K$_i$≤0.1 nM), B represents a pK$_i$ value between 9 and 10 (K$_i$ between 1 nM and 0.1 nM), C represents a pK$_i$ value between 8 and 9 (K$_i$ between 10 nM and 1 nM), D represents a pK$_i$ value between 7 and 8 (K$_i$ between 100 nM and 10 nM), and E represents a pK$_i$ value of 7 or below (K$_i$ of 100 nM or above). For the Tall-1 Potency assay, A represents a pIC$_{50}$ value ≥8.0, and B represents a pIC$_{50}$ value between 7.5 (included) and 8.0.

TABLE 1

| | JAK 1 (pKi) | JAK 2 (pKi) | JAK 3 (pKi) | Tyk 2 (pKi) | Tall-1 IL2 pSTAT5 (pIC$_{50}$) |
|---|---|---|---|---|---|
| M | A | A | B | B | A |
| 1 | B | A | B | A | A |
| 2 | B | | B | | A |
| 3 | B | | C | | A |
| 4 | B | | C | | A |
| 5 | C | | D | | A |
| 6 | C | B | D | C | B |
| 7 | B | A | B | A | A |
| 8 | B | | C | | A |
| 9 | B | A | C | B | A |

Assay 3: Human Liver Microsome Assay

The objective of this assay was to assess the metabolic stability of test compounds in an in vitro human liver sub-fraction. Human liver microsomes obtained from Bioreclamation-IVT (Baltimore, Md.) were thawed on ice and diluted into 0.1M potassium phosphate buffer pH 7.4 to yield final incubation protein concentrations of 0.1 mg/mL. Test compounds (10 mM) were diluted into NADPH cofactor to yield final incubation concentrations of 0.1 µM test compound and 1 mM NADPH. Incubations were conducted at 37° C. temperature and test aliquots were taken at time points 0, 5, 8, 15, 30 and 45 minutes. Each aliquot was crashed into water with 3% formic acid and 1 µM internal standard. The resulting samples were injected onto an LC-MS/MS system for analysis.

For each incubation, the peak area of the analytes in each t0 aliquot was set to 100% and the peak areas from subsequent time point aliquots were converted to percentage of parent compound remaining relative to t0. The percentage of parent compound remaining was converted to natural log scale and plotted versus time in minutes. A linear regression analysis was performed for the initial decline of the parent disappearance profile and a formula for the best-fit line determined. The slope of the resultant line was normalized to protein concentration in mg/mL protein or number of cells/mL and CL$_{int}$ was calculated as follows for liver microsomes:

$$CL_{int}(\mu L \cdot min^{-1} \cdot mg^{-1}) = (Slope \times 1000)/[protein, mg/mL]$$

CL$_{int}$ values from 0-8 µl/min/mg represent low clearance (i.e <30% of hepatic blood flow in human). CL$_{int}$ values from 9-49 µl/min/mg represent moderate clearance (i.e. 30-70% of hepatic blood flow in human) and values >50 µl/min/mg represent high hepatic clearance (i.e. >70% of hepatic blood flow in human).

Compound M exhibited a HLM Cl$_{int}$ of 132 µL/min/mg. Compounds 7 and 9 exhibited a HLM Cl$_{int}$ over 2500 µL/min/mg.

Assay 4: Aqueous Solubility Assay

The purpose of this assay was to quantify the solubility of test compounds in pH 4 and pH 7.4 PBS buffers. The assay required 40 µL of 10 mM DMSO test compound solution per desired buffer in addition to 20 µL required to make a test standard. For example, to test a compound in both buffers, 100 µL (2*40 µL+20 µL) of 10 mM DMSO compound stock solution was required.

The standard was created by diluting 20 µL of 10 mM DMSO compound stock solution into 180 µL of methanol and was shaken for five minutes to ensure solution uniformity. The resulting solution had a concentration of 1 mM, or 1,000 µM, of the test compound. This 1,000 µM solution was run on an Agilent 1260 LC-MS system by injecting 2 µL in order to obtain the peak area. For the test solutions, 40 µL of 10 mM DMSO compound stock solution, per PBS buffer condition, were dried down into a powder overnight. Once in powder form, 400 µL of the desired PBS buffer was added to the powder and allowed to shake vigorously for four hours. The maximum theoretical concentration for this sample solution was 1,000 µM. After four hours of shaking, the samples were centrifuged for 10 minutes at 3,000 RPM before injecting 2 µL on the same Agilent 1260 LC-MS system to obtain the peak area. Once the peak areas for the standard and the test solution were determined, the ratio of sample area to standard area*1,000 yielded the µM solubility of the test compound solution, with a maximum upper limit of 1,000 µM. Table 2 summarizes the results obtained.

In Table 2 below, A represents a value above 100, B represents a value between 100 and 50 (included), C represents a value between 50 and 10 and D represents a value of 10 or below.

TABLE 2

| | Solubility at PH 7.4 (µmol) |
|---|---|
| M | C |
| 1 | C |
| 2 | C |
| 3 | C |
| 4 | B |
| 5 | C |
| 7 | A |
| 6 | C |
| 9 | A |
| 8 | B |

Assay 5: Solubility Assay in Organic Excipients

The purpose of this assay was to quantify the solubility of test compounds in different organic excipients such as diisopropyl adipate, medium chain triglycerides (MCT), propylene glycol, and polyethylene glycol. The assay required 80 µL of 100 mM DMSO test compound solution per desired excipient in addition to 40 µL required to make a test standard. For example, to test a compound in all five excipients, 440 µL (5*80 µL+40 µL) of 100 mM DMSO compound stock solution was required.

The standard was created by diluting 40 µL of 100 mM DMSO compound stock solution into 160 µL of methanol and was shaken for five minutes to ensure solution uniformity. The resulting solution had a concentration of 20 mM, or 20,000 µM of the test compound. This 20,000 µM solution was run on an Agilent 1260 LC-MS system by injecting 0.2 µL in order to obtain the peak area. For the test solutions, 80 µL of 100 mM DMSO compound stock solution, per excipient, were dried down into a powder overnight. Once in powder form, 400 µL of the desired excipient was added to the powder and allowed to shake vigorously for four hours. The maximum theoretical concentration for this sample solution was 20,000 µM. After four hours of shaking, the samples were centrifuged for 10 minutes at 3,000 RPM before injecting 0.2 µL on the same Agilent 1260 LC-MS system to obtain the peak area. Once the peak areas for the standard and the test solution were determined, the ratio of sample area to standard area*20,000 yielded the µM solubility of the test compound solution, with a maximum upper limit of 20,000 µM. Table 3 summarizes the results obtained.

In Table 3 below, A represents a value above 10, B represents a value between 5 and 10, C represents a value below 5.

TABLE 3

| | Diisopropyl adipate (mg/mL) | Transcutol (mg/mL) | MCT (mg/mL) | Propylene glycol (mg/mL) | PEG400 (mg/mL) |
|---|---|---|---|---|---|
| M | C | A | C | C | C |
| 1 | A | A | C | A | B |
| 2 | A | A | C | A | A |
| 3 | A | A | C | A | A |
| 4 | A | A | C | C | A |
| 5 | A | A | C | B | A |
| 6 | A | A | C | B | B |
| 7 | A | | C | A | A |
| 8 | A | | C | C | A |
| 9 | A | | C | A | A |

Assay 6: In Vitro Skin S9 Metabolic Stability Assay

The objective of this assay was to assess the metabolic stability of compounds in human and mouse skin S9 sub-fraction. Human and mouse skin S9 sub-fractions obtained from Bioreclamation-IVT (Baltimore, Md.) were thawed on ice and diluted into 0.1M potassium phosphate buffer pH 7.4 to yield final incubation protein concentrations of 1.0 mg/mL. Test compounds (10 mM) were diluted into phosphate buffer to yield final incubation concentrations of 0.2 µM and 2.0 µM. Incubations were conducted at 37° C. temperature following addition of 1 mM NADPH and test aliquots were taken at time points 0, 5, 10, 20, 30 and 45 minutes. Each aliquot was crashed into water with 3% formic acid and 1 µM internal standard. The resulting samples were injected onto an LC-MS/MS system for analysis.

For each incubation, the peak area of the analytes in each t0 aliquot was set to 100% and the peak areas from subsequent time point aliquots were converted to percentage of parent compound remaining relative to t0. The percentage of parent compound remaining at each time point was converted to natural log scale and plotted versus time in minutes to determine a disappearance half-life. The active metabolite M was also monitored by LC-MS in each incubation in order to demonstrate corresponding appearance of compound M to disappearance of the parent compound. All test compounds showed release of the active metabolite M. In Table 4, the stability of compounds was assigned as follows: +++ corresponds to a half-life <15 minutes, ++ corresponds to a half-life between 15 and 30 minutes, and + corresponds to a half-life >30 minutes.

TABLE 4

| | | Half-Life (min) | |
|---|---|---|---|
| Compound | Skin S9 | 0.2 µM | 2 µM |
| 7-Ethoxycoumarin | Human | + | + |
| 7-Ethoxycoumarin | Mouse | + | + |
| Benfluorex | Human | +++ | +++ |
| Benfluorex | Mouse | +++ | +++ |
| 1 | Human | + | + |
| 1 | Mouse | +++ | ++ |
| 2 | Human | + | + |
| 2 | Mouse | ++ | ++ |
| 3 | Human | + | + |
| 3 | Mouse | +++ | +++ |
| 4 | Human | ++ | + |
| 4 | Mouse | +++ | +++ |
| 6 | Human | + | + |
| 6 | Mouse | +++ | +++ |

Assay 7: Topical Pharmacokinetics Assay

The objective of this Study was to determine the epidermal, dermal and plasma pharmacokinetics of test compounds following 24 hours of topical exposure to intact male rat skin. Test compounds were formulated to 0.25% (w/w) in ointment as described in Table 5.

TABLE 5

Formulations of Test Compounds
Formulation (ointment)

| Test compound | 0.25% |
|---|---|
| Octylhydroxystearate | 5% |
| C8-C10 Triglyceride | 5% |
| Vaseline (Petrolatum) | 79.75% |
| N-Methylpyrrolidone | 10% |

Twenty-four hours prior to dosing, the hair was shaved from the back of 250 g male Sprague Dawley rats exposing an area 4×5 cm of at least 20 cm² (about 10% of body surface). At time zero, test compound was applied to the back of the rats at a dose of 25 μL/cm². The skin was covered with an adhesive cover to prevent loss of compound to the cage or bedding. Following 0.5, 2.6 and 24 h exposure, the backs were gently washed with soap and water to remove non-absorbed drug and patted dry. Immediately following this washing, blood was drawn by cardiac puncture from the rats. The outer skin (stratum corneum) was then removed by adhesive tape stripping. Upon exposure of the epidermis a 0.5 cm punch biopsy was taken. The epidermis and dermis were quickly separated, weighed and snap frozen. Epidermis and dermis samples were homogenized in 1:10 (w/v) water using a Covaris ultrasonic homogenizer. Samples were extracted in 3 volumes of acetonitrile and quantified against a standard curve via LC-MS analysis for test compound or active metabolite M. To determine the extent of conversion of test compound to active metabolite M, the sum of the AUC of test compound and active metabolite M in epidermis, dermis and plasma was determined and expressed as '% conversion' (i.e. ratio of active metabolite M/test compound×100). Compounds 7 and 9 exhibited a conversion over 30% in this assay.

Assay 8: Caco-2 Permeation Assay

The Caco-2 permeation assay was used as an indication of skin permeability. The assay measures the rate at which test compounds in solution permeate a cell monolayer (designed to mimic the tight junction of human small intestinal monolayers).

CacoReady 24-well transwell plates were obtained from ADMEcell (Alameda, Calif.). The compounds were evaluated at a concentration of 5 μM from 10 mM DMSO stock solutions in duplicate (n=2). The passive permeability of the compounds tested was evaluated using Caco-2 cell monolayers along with Verapamil (25 μM) to inhibit P-gp transport proteins in the apical to basolateral (A-B) direction. The experiment was conducted in a 37° C., 5% $CO_2$ incubator. Caco-2 culture media consisted of standard filtered DMEM, FCS 10%, L-Glutamine 1% and PenStrep 1%. Basal assay plate was prepared by adding 750 μL of transport buffer to A-B wells. A CacoReady™ plate was prepared by removing the Caco-2 media from the apical wells and replacing with fresh transport media (200 μL repeated for a total of 3 washes). Blank media (200 μL) was then replaced with diluted compound for A-B wells. To begin the incubation, the basal plate was removed from the incubator and the apical section was added on top of it. Samples (40 μL) were collected from the apical and basal compartments for time zero (t0). Samples were collected again after 120 minutes (t120) from the apical and basal compartments. All samples were diluted and prepared for bioanalysis by LC-MS/MS.

The permeation coefficient ($K_p$, mean A to B+Verapamil Papparent) in cm/sec was calculated as dQ (flux)/(dt×Area× concentration).

In this assay, a compound with a $K_p$ value of less than about $5 \times 10^{-6}$ cm/sec is considered to have low permeability. A compound having a $K_p$ value of more than about $20 \times 10^{-6}$ cm/sec is considered to have high permeability.

Characterization of Compound M and Comparison Compounds

TABLE 6

Characterization of comparison compounds

| Compound # | Structure | $Caco_{verap}$ $K_p$ $10^{-6}$ cm/sec | HLM $Cl_{int}$ μL/min/mg |
|---|---|---|---|
| M | (structure) | 42.3 | 136 |
| C-1 | (structure) | 3.55 | 6 |
| C-2 | (structure) | 5.5 | 12 |

Comparative compounds C-1 and C-2 were disclosed by applicant in some presentations made in April, June and August 2017 at conferences.

59

Compound M is characterized by a much higher permeability (Caco$_{verap}$ value) and human liver microsome clearance (HLM Cl$_{int}$ value) than C-1 and C-2. A higher clearance is beneficial to promote quick systemic clearance and prevent systemic exposure which may be associated with side effects. Higher permeability is beneficial for skin indications as it appears to provide for better penetration in the skin.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A pharmaceutical composition comprising a compound selected from the group consisting of:

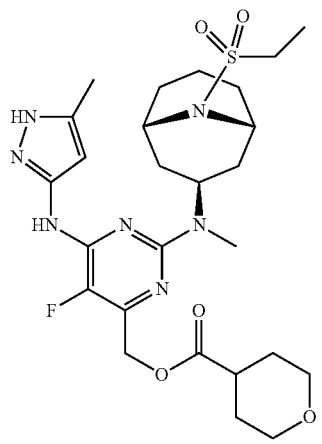

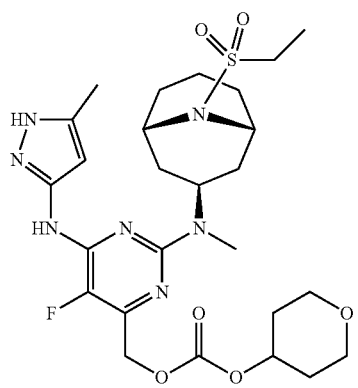

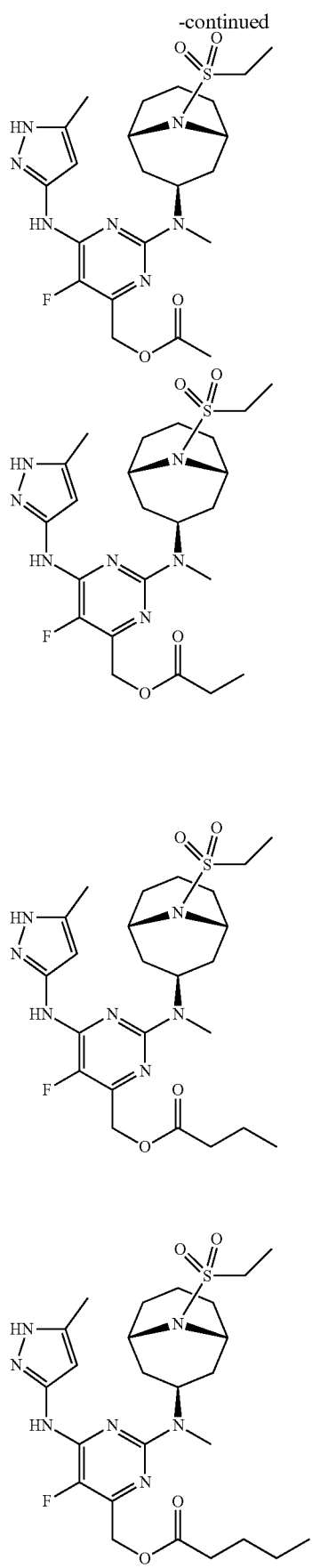

-continued

-continued

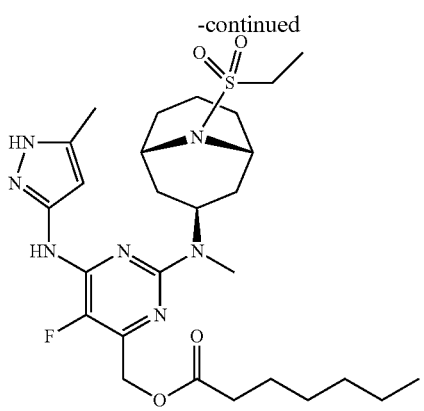

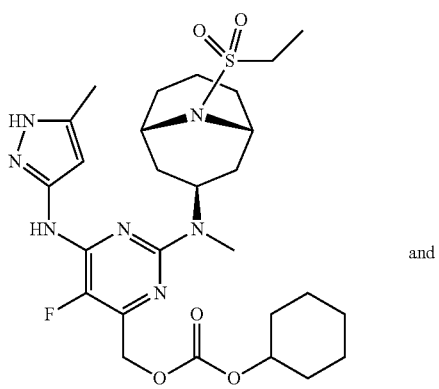
and

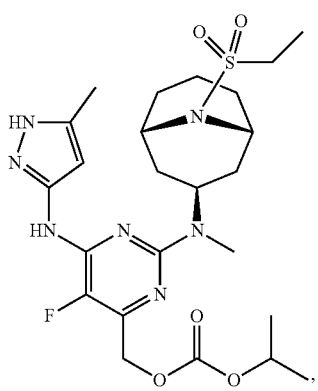 [SMILES: CCS(=O)(=O)N1[C@@H]2CCC[C@H]1C[C@H](N(C)c1nc(COC(=O)OC(C)C)c(F)c(Nc3cc(C)[nH]n3)n1)C2]

or a pharmaceutically acceptable salt thereof, and a pharmaceutically-acceptable carrier.

2. The pharmaceutical composition of claim 1, wherein the compound is a compound of formula:

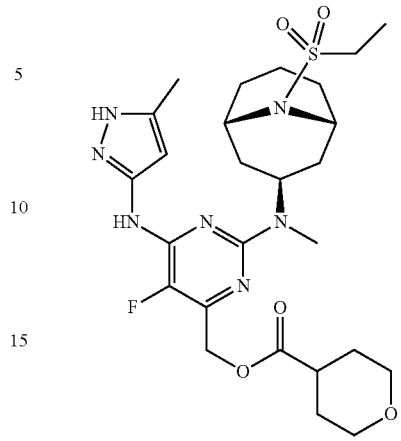

or a pharmaceutically acceptable salt thereof.

3. The pharmaceutical composition of claim 1, wherein the compound is a compound of formula:

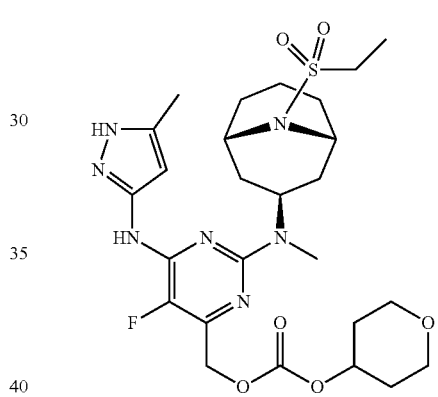

or a pharmaceutically acceptable salt thereof.

4. The pharmaceutical composition of claim 1, further comprising one or more additional therapeutic agents.

5. The pharmaceutical composition of claim 1, wherein the pharmaceutical composition is selected from the group consisting of a lotion, cream, gel, stick, spray, ointment, paste, foam, and mousse.

6. The pharmaceutical composition of claim 5, wherein the pharmaceutical composition is a lotion.

7. The pharmaceutical composition of claim 5, wherein the pharmaceutical composition is a cream.

8. The pharmaceutical composition of claim 5, wherein the pharmaceutical composition is a gel.

9. The pharmaceutical composition of claim 5, wherein the pharmaceutical composition is a stick.

10. The pharmaceutical composition of claim 5, wherein the pharmaceutical composition is a spray.

11. The pharmaceutical composition of claim 5, wherein the pharmaceutical composition is an ointment.

12. The pharmaceutical composition of claim 5, wherein the pharmaceutical composition is a paste.

13. The pharmaceutical composition of claim 5, wherein the pharmaceutical composition is a foam.

14. The pharmaceutical composition of claim 5, wherein the pharmaceutical composition is a mousse.

15. The pharmaceutical composition of claim 1, wherein the compound, or a pharmaceutically acceptable salt thereof, is present at between 0.1 and 10% by weight.

16. The pharmaceutical composition of claim 1, wherein the compound, or a pharmaceutically acceptable salt thereof, is present at between 0.25 and 5% by weight.

17. The pharmaceutical composition of claim 1, wherein the compound, or a pharmaceutically acceptable salt thereof, is present at between 0.05 and 0.5% by weight.

* * * * *